(12) United States Patent
Sheng

(10) Patent No.: US 12,295,758 B2
(45) Date of Patent: May 13, 2025

(54) SUPINE BREAST CT SCANNER

(71) Applicant: THE REGENTS OF THE UNIVERSITY OF CALIFORNIA, Oakland, CA (US)

(72) Inventor: Ke Sheng, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 361 days.

(21) Appl. No.: 17/759,766

(22) PCT Filed: Feb. 2, 2021

(86) PCT No.: PCT/US2021/016233
§ 371 (c)(1),
(2) Date: Jul. 29, 2022

(87) PCT Pub. No.: WO2021/158558
PCT Pub. Date: Aug. 12, 2021

(65) Prior Publication Data
US 2023/0060834 A1    Mar. 2, 2023

Related U.S. Application Data
(60) Provisional application No. 62/969,402, filed on Feb. 3, 2020.

(51) Int. Cl.
*A61B 6/03* (2006.01)
*A61B 6/04* (2006.01)
(Continued)

(52) U.S. Cl.
CPC ............ *A61B 6/032* (2013.01); *A61B 6/0435* (2013.01); *A61B 6/4085* (2013.01); *A61B 6/502* (2013.01);
(Continued)

(58) Field of Classification Search
CPC ....... A61B 6/032; A61B 6/0435; A61B 6/502; A61B 90/17; A61B 6/4085; A61B 6/0414;
(Continued)

(56) References Cited

U.S. PATENT DOCUMENTS

| | | |
|---|---|---|
| 6,463,122 B1 | 10/2002 | Moore |
| 7,676,021 B2 | 3/2010 | Tsujii |

(Continued)

FOREIGN PATENT DOCUMENTS

| | | |
|---|---|---|
| JP | 6381253 | 8/2018 |
| WO | 2017173341 | 10/2017 |

OTHER PUBLICATIONS

Tanner C, Degenhard A, Schnabel JA, Smith AC, Hayes C, Sonoda LI, Leach MO, Hose DR, Hill DLG, Hawkes DJ. A method for the comparison of biomechanical breast models. Ieee Workshop on Mathematical Methods in Biomedical Image Analysis, Proceedings. 2001:11-8. doi: Doi 10.1109/Mmbia.2001.991694. PubMed PMID: WOS:000173392800002.

(Continued)

*Primary Examiner* — Congvan Tran
(74) *Attorney, Agent, or Firm* — Riverside Law LLP

(57) ABSTRACT

A cone beam CT scanner comprises a receiving section configured to receive a breast of the subject whilst in the supine position, a radiation imaging section comprising an x-ray tube and a detector which face each other and have the receiving section interposed therebetween, and a drive unit operable to move the receiving section to a position suitable for imaging the breast of the subject. A method for breast radiography is also disclosed.

22 Claims, 11 Drawing Sheets

(51) Int. Cl.
  *A61B 6/40* (2024.01)
  *A61B 6/50* (2024.01)
  *A61B 90/17* (2016.01)
  *A61B 34/20* (2016.01)
  *A61B 90/00* (2016.01)

(52) U.S. Cl.
  CPC ...... *A61B 90/17* (2016.02); *A61B 2034/2051* (2016.02); *A61B 2034/2055* (2016.02); *A61B 2034/2059* (2016.02); *A61B 2090/3762* (2016.02)

(58) Field of Classification Search
  CPC .... A61B 2034/2059; A61B 2034/2055; A61B 2034/2046; A61B 2090/3762; A61B 2034/2051
  See application file for complete search history.

(56) References Cited

U.S. PATENT DOCUMENTS

| | | | |
|---|---|---|---|
| 7,957,503 B2 | 6/2011 | Kobayashi | |
| 9,629,597 B2 | 4/2017 | Vedantham | |
| 9,913,689 B2 | 3/2018 | Sheng | |
| 10,959,697 B2* | 3/2021 | Richard | H04N 23/30 |
| 11,488,313 B2* | 11/2022 | Alzaga | A61B 5/7285 |
| 11,903,751 B2* | 2/2024 | Helm | A61B 6/5241 |
| 2005/0207526 A1* | 9/2005 | Altman | A61B 6/032 378/20 |
| 2006/0009693 A1 | 1/2006 | Hanover | |
| 2006/0182219 A1* | 8/2006 | Levy | G01N 23/04 378/62 |
| 2007/0050908 A1 | 3/2007 | Kogan | |
| 2008/0267484 A1* | 10/2008 | Chen | G06T 11/006 382/132 |
| 2009/0022269 A1 | 1/2009 | Tsujii | |
| 2009/0129556 A1* | 5/2009 | Ahn | A61N 5/1049 378/208 |
| 2010/0177866 A1 | 7/2010 | Shibuya | |
| 2014/0037044 A1* | 2/2014 | Ning | A61B 6/463 378/4 |
| 2014/0148686 A1 | 5/2014 | Thevathasan | |
| 2015/0131776 A1 | 5/2015 | Cho | |
| 2015/0272682 A1 | 10/2015 | Sheng | |
| 2017/0238897 A1* | 8/2017 | Siewerdsen | A61B 6/466 |
| 2018/0214139 A1* | 8/2018 | Yan | A61B 34/20 |
| 2020/0121267 A1* | 4/2020 | Deutschmann | A61B 6/4452 |
| 2020/0219253 A1* | 7/2020 | Magaraggia | A61B 34/37 |

OTHER PUBLICATIONS

Tanner C, Hipwell JH, Hawkes DJ. Statistical deformation models of breast compressions from biomechanical simulations. Digital Mammography, Proceedings. 2008;5116:426-32. PubMed PMID: WOS:000258502700059.

Trinh, H. et al., 2011, Journal of electronic science and technology, 10(2):1-6.

Vallier S, Troccaz J, Gabelle-Flandin I, Payan Y. Biomechanical breast modelling to improve patient positioning during breast cancer radiotherapy. Comput Method Biomec. 2013;16:278-9. doi: 10.1080/10255842.2013.815862. PubMed PMID: WOS:000322818100118.

Van Nierop BJ, Prince JF, van Rooij R, van den Bosch M, Lam M, de Jong H. Accuracy of SPECT/CT-based lung dose calculation for Holmium-166 hepatic radioembolization before OSEM convergence. Medical physics. 2018. doi: 10.1002/mp.13024. PubMed PMID: 29858506; PubMed Central PMCID: PMC6099428.

Vedantham S, Karellas A, Emmons MM, Moss LJ, Hussain S, Baker SP. Dedicated breast CT: geometric design considerations to maximize posterior breast coverage. Physics in medicine and biology. 2013;58(12):4099-118. doi: 10.1088/0031-9155/58/12/4099. PubMed PMID: 23685899; PubMed Central PMCID: PMC3711264.

Vedantham S, O'Connell AM, Shi L, Karellas A, Huston AJ, Skinner KA. Dedicated Breast CT: Feasibility for Monitoring Neoadjuvant Chemotherapy Treatment. Journal of clinical imaging science. 2014;4:64. doi: 10.4103/2156-7514.145867. PubMed PMID: 25558431; PubMed Central PMCID: PMC4278089.

Vedantham S, Shi L, Karellas A, Noo F. Dedicated breast CT: radiation dose for circle-plus-line trajectory. Medical physics. 2012;39(3):1530-41. doi: 10.1118/1.3688197. PubMed PMID: 22380385; PubMed Central PMCID: PMC3306439.

Vedantham S, Shi L, Karellas A, O'Connell AM. Dedicated breast CT: fibroglandular volume measurements in a diagnostic population. Medical physics. 2012;39(12):7317-28. doi: 10.1118/1.4765050. PubMed PMID: 23231281; PubMed Central PMCID: PMC3524966.

Venkatakrishnan, S. et al., 2013, IEEE Glob. Conf. Sig., 945-948.

Vermeulen S, Cotrutz C, Morris A, Meier R, Buchanan C, Dawson P, Porter B. Accelerated Partial Breast Irradiation: Using the CyberKnife as the Radiation Delivery Platform in the Treatment of Early Breast Cancer. Frontiers in oncology. 2011;1:43. doi: 10.3389/fonc.2011.00043. PubMed PMID: 22649764; PubMed Central PMCID: PMC3355980.

Vermeulen SS, Haas JA. CyberKnife stereotactic body radiotherapy and CyberKnife accelerated partial breast irradiation for the treatment of early breast cancer. Transl Cancer Res. 2014;3(4):295-302. doi: 10.3978/j.issn.2218-676X.2014.07.06. PubMed PMID: WOS:000209643800002.

Veronesi U, Cascinelli N, Mariani L, Greco M, Saccozzi R, Luini A, Aguilar M, Marubini E. Twenty-year follow-up of a randomized study comparing breast-conserving surgery with radical mastectomy for early breast cancer. New Engl J Med. 2002;347(16):1227-32. doi: Doi 10.1056/Nejmoa020989. PubMed PMID: WOS:000178598300003.

Wade TD, Zhu G, Martin NG. Body mass index and breast size in women: same or different genes? Twin research and human genetics : the official journal of the International Society for Twin Studies. 2010;13(5):450-4. doi: 10.1375/twin.13.5.450. PubMed PMID: 20874466.

Wang, X.R. et al., 2017, IEEE International Conference on Acoustics, Speech and Signal Processing (Icassp):1323-7.

Wessel C, Schnabel JA, Brady M. Realistic Biomechanical Model of a Cancerous Breast for the Registration of Prone to Supine Deformations. Ieee Eng Med Bio. 2013:7249-52. PubMed PMID: WOS:000341702107158.

Wessel C, Schnabel JA, Brady M. Towards a more realistic biomechanical modelling of breast malignant tumours. Physics in medicine and biology. 2012;57(3):631-48. doi: 10.1088/0031-9155/57/3/631. PubMed PMID: WOS:000299542000006.

West Virginia University School of Medicine. (n.d.). Breast Pet-CT imaging and biopsy system. Breast PET-CT Imaging and Biopsy System | School of Medicine | West Virginia University. https://medicine.hsc.wvu.edu/radio/research/breast-pet-ct-imaging-and-biopsy-system/.

Whelan T, MacKenzie R, Julian J, Levine M, Shelley W, Grimard L, Lada B, Lukka H, Perera F, Fyles A, Laukkanen E, Gulavita S, Benk V, Szechtman B. Randomized trial of breast irradiation schedules after lumpectomy for women with lymph node-negative breast cancer. J Natl Cancer I. 2002;94(15):1143-50. PubMed PMID: WOS:000177231100011.

Whelan TJ, Levine M, Julian J, Kirkbride P, Skingley P, Grp OCO. The effects of radiation therapy on quality of life of women with breast carcinoma—Results of a randomized trial. Cancer. 2000;88(10):2260-6. doi: Doi 10.1002/(Sici) 1097-0142(May 15, 2000)88:10<2260::Aid-Cncr9>3.0.Co;2-M. PubMed PMID: WOS:000086810500009.

Wu, P. et al., 2018, Soft robotics, 5(1):71-80.

Xu Q, Chen Y, Grimm J, Fan J, An L, Xue J, Pahlajani N, Lacouture T. Dosimetric investigation of accelerated partial breast irradiation (APBI) using CyberKnife. Medical physics. 2012;39(11):6621-8. doi: 10.1118/1.4757616. PubMed PMID: 23127056.

Yang WT, Carkaci S, Chen L, Lai CJ, Sahin A, Whitman GJ, Shaw CC. Dedicated cone-beam breast CT: feasibility study with surgical mastectomy specimens. AJR American journal of roentgenology.

(56) References Cited

OTHER PUBLICATIONS

2007;189(6):1312-5. doi: 10.2214/AJR.07.2403. PubMed PMID: 18029864; PubMed Central PMCID: PMC2856818.
Yashar CM, Scanderbeg D, Kuske R, Wallace A, Zannis V, Blair S, Grade E, Swenson VH, Quiet C. Initial clinical experience with the Strut-Adjusted Volume Implant (SAVI) breast brachytherapy device for accelerated partial-breast irradiation (APBI): first 100 patients with more than 1 year of follow-up. International journal of radiation oncology, biology, physics. 2011;80(3):765-70. doi: 10.1016/j.ijrobp.2010.02.018. PubMed PMID: 20646847.
Yu CX, Shao X, Zhang J, Regine W, Zheng M, Yu YS, Deng J, Duan Z. GammaPod—a new device dedicated for stereotactic radiotherapy of breast cancer. Medical physics. 2013;40(5):051703. doi: 10.1118/1.4798961. PubMed PMID: 23635251; PubMed Central PMCID: PMC3637326.
Yu W, Wang C, Nie X, Zeng D. Sparsity-induced dynamic guided filtering approach for sparse-view data toward low-dose x-ray computed tomography. Physics in medicine and biology. 2018;63(23):235016. doi: 10.1088/1361-6560/aaeea6. PubMed PMID: 30484434.
Zhang, K. et al., 2017, IEEE T Comput. Imag., 26(7):3142-55.
Zhou Z, Guan S, Xin R, Li J. Investigation of contrast-enhanced subtracted breast CT images with MAP-EM based on projection-based weighting imaging. Australasian physical & engineering sciences in medicine. 2018;41(2):371-7. doi: 10.1007/s13246-018-0634-y. PubMed PMID: 29637425.
Beck, A. et al., 2009, Siam J Imaging Sci., 2(1):183-202.
Bentel GC, Marks LB. A simple device to position large/flaccid breasts during tangential breast irradiation. International journal of radiation oncology, biology, physics. 1994;29(4):879-82. PubMed PMID: 8040038.
Berry DA, Cronin KA, Plevritis SK, Fryback DG, Clarke L, Zelen M, Mandelblatt JS, Yakovlev AY, Habbema JD, Feuer EJ, Cancer I, Surveillance Modeling Network C. Effect of screening and adjuvant therapy on mortality from breast cancer. The New England journal of medicine. 2005;353(17):1784-92. doi: 10.1056/NEJMoa050518. PubMed PMID: 16251534.
Bian J, Yang K, Boone JM, Han X, Sidky EY, Pan X. Investigation of iterative image reconstruction in low-dose breast CT. Physics in medicine and biology. 2014;59(11):2659-85. doi: 10.1088/0031-9155/59/11/2659. PubMed PMID: 24786683; PubMed Central PMCID: PMC4104195.
Boone JM, Hendee WR, McNitt-Gray MF, Seltzer SE. Radiation exposure from CT scans: how to close our knowledge gaps, monitor and safeguard exposure—proceedings and recommendations of the Radiation Dose Summit, sponsored by NIBIB, Feb. 24-25, 2011. Radiology. 2012;265(2):544-54. doi: 10.1148/radiol.12112201. PubMed PMID: 22966066; PubMed Central PMCID: PMC3480815.
Boone, J.M. et al., 2001, Radiology, 221(3)657-67.
Boyd, S., 2011, Proc 51st IEEE Conf. Decis. Cont., 3(1):1-44.
Cai A, Li L, Zheng Z, Wang L, Yan B. Block-matching sparsity regularization-based image reconstruction for low-dose computed tomography. Medical physics. 2018;45(6):2439-52. doi: 10.1002/mp.12911. PubMed PMID: 29645279.
Calisti M, Picardi G, Laschi C. Fundamentals of soft robot locomotion. Journal of the Royal Society, Interface. 2017;14(130). doi: 10.1098/rsif.2017.0101. PubMed PMID: 28539483; PubMed Central PMCID: PMC5454300.
Charaghvandi RK, Yoo S, van Asselen B, Rodrigues A, van den Bongard D, Horton JK. Treatment constraints for single dose external beam preoperative partial breast irradiation in early-stage breast cancer. Clinical and translational radiation oncology. 2017;6:7-14. doi: 10.1016/j.ctro.2017.06.003. PubMed PMID: 29594217; PubMed Central PMCID: PMC5862640.
Chen H, Zhang Y, Chen Y, Zhang J, Zhang W, Sun H, Lv Y, Liao P, Zhou J, Wang G. Learn: Learned Experts' Assessment-Based Reconstruction Network for Sparse-Data CT. IEEE Trans Med Imaging. 2018;37(6):1333-47. doi: 10.1109/TMI.2018.2805692. PubMed PMID: 29870363; PubMed Central PMCID: PMC6019143.
Cockmartin, L. et al., 2013, Medical Physics, 40(8):081920.
Csenki M, Ujhidy D, Cserhati A, Kahan Z, Varga Z. Radiation dose to the nodal regions during prone versus supine breast irradiation. Therapeutics and clinical risk management. 2014;10:367-72. doi: 10.2147/TCRM.S59483. PubMed PMID: 24876782; PubMed Central PMCID: PMC4038347.
Curtis RE, Boice JD, Jr., Stovall M, Bernstein L, Greenberg RS, Flannery JT, Schwartz AG, Weyer P, Moloney WC, Hoover RN. Risk of leukemia after chemotherapy and radiation treatment for breast cancer. The New England journal of medicine. 1992;326(26):1745-51. doi: 10.1056/NEJM199206253262605. PubMed PMID: 1594016.
Dabov, K. et al., 2007, IEEE T Image Process, 16(8):2080-95.
Darby SC, Ewertz M, McGale P, Bennet AM, Blom-Goldman U, Bronnum D, Correa C, Cutter D, Gagliardi G, Gigante B, Jensen MB, Nisbet A, Peto R, Rahimi K, Taylor C, Hall P. Risk of ischemic heart disease in women after radiotherapy for breast cancer. The New England journal of medicine. 2013;368(11):987-98. doi: 10.1056/NEJMoa1209825. PubMed PMID: 23484825.
Diekmann F. Contrast-enhanced dedicated breast CT. Radiology. 2011;258(2):650; author reply—1. doi: 10.1148/radiol.101761. PubMed PMID: 21273529.
Ding H, Gao H, Zhao B, Cho HM, Molloi S. A high-resolution photon-counting breast CT system with tensor-framelet based iterative image reconstruction for radiation dose reduction. Physics in medicine and biology. 2014;59(20):6005-17. doi: 10.1088/0031-9155/59/20/6005. PubMed PMID: 25230204; PubMed Central PMCID: PMC5219880.
Dore M, Hennequin C. [Late sequelae and cosmetic outcome after radiotherapy in breast conserving therapy]. Cancer radiotherapie : journal de la Societe francaise de radiotherapie oncologique. 2012;16(5-6):462-9. doi: 10.1016/j.canrad.2012.05.018. PubMed PMID: 22925491.
Fisher B, Anderson S, Bryant J, Margolese RG, Deutsch M, Fisher ER, Jeong J, Wolmark N. Twenty-year follow-up of a randomized trial comparing total mastectomy, lumpectomy, and lumpectomy plus irradiation for the treatment of invasive breast cancer. New Engl J Med. 2002;347(16):1233-41. doi: Doi 10.1056/Nejmoa022152. PubMed PMID: WOS:000178598300004.
Fisher B, Anderson S, Bryant J, Margolese RG, Deutsch M, Fisher ER, Jeong JH, Wolmark N. Twenty-year follow-up of a randomized trial comparing total mastectomy, lumpectomy, and lumpectomy plus irradiation for the treatment of invasive breast cancer. The New England journal of medicine. 2002;347(16):1233-41. doi: 10.1056/NEJMoa022152. PubMed PMID: 12393820.
Formenti SC, DeWyngaert JK, Jozsef G, Goldberg JD. Prone vs supine positioning for breast cancer radiotherapy. Jama. 2012;308(9):861-3. doi: 10.1001/2012.jama.10759. PubMed PMID: 22948692.
Garcia E, Diez Y, Diaz O, Llado X, Marti R, Marti J, Oliver A. A step-by-step review on patient-specific biomechanical finite element models for breast MRI to x-ray mammography registration. Medical physics. 2018;45(1):e6-e31. doi: 10.1002/mp.12673. PubMed PMID: WOS:000419961400002.
Goggin LM, Descovich M, McGuinness C, Shiao S, Pouliot J, Park C. Dosimetric Comparison Between 3-Dimensional Conformal and Robotic SBRT Treatment Plans for Accelerated Partial Breast Radiotherapy. Technology in cancer research & treatment. 2016;15(3):437-45. doi: 10.1177/1533034615601280. PubMed PMID: 26335703.
Gu C, Zeng D, Lin J, Li S, He J, Zhang H, Bian Z, Niu S, Zhang Z, Huang J, Chen B, Zhao D, Chen W, Ma J. Promote quantitative ischemia imaging via myocardial perfusion CT iterative reconstruction with tensor total generalized variation regularization. Physics in medicine and biology. 2018;63(12):125009. doi: 10.1088/1361-6560/aac7bd. PubMed PMID: 29794346.
Ha S, Mueller K. A Look-Up Table-Based Ray Integration Framework for 2-D/3-D Forward and Back Projection in X-Ray CT. IEEE Trans Med Imaging. 2018;37(2):361-71. doi: 10.1109/TMI.2017.2741781. PubMed PMID: 28829308.
Hajash K, Sparrman B, Guberan C, Laucks J, Tibbits S. Large-Scale Rapid Liquid Printing. 3d Print Addit Manuf. 2017;4(3):123-31. doi: 10.1089/3dp.2017.0037. PubMed PMID: WOS:000413593200002.
Hamilton DG, Bale R, Jones C, Fitzgerald E, Khor R, Knight K, Wasiak J. Impact of tumour bed boost integration on acute and late

(56) References Cited

OTHER PUBLICATIONS toxicity in patients with breast cancer: A systematic review. Breast. 2016;27:126-35. doi: 10.1016/j.breast.2016.03.002. PubMed PMID: 27113229.

Han LH, Hipwell JH, Eiben B, Barratt D, Modat M, Ourselin S, Hawkes DJ. A Nonlinear Biomechanical Model Based Registration Method for Aligning Prone and Supine MR Breast Images. Ieee T Med Imaging. 2014;33(3):682-94. doi: 10.1109/Tmi.2013.2294539. PubMed PMID: WOS:000332599500007.

Han LH, Hipwell JH, Tanner C, Taylor Z, Mertzanidou T, Cardoso J, Ourselin S, Hawkes DJ. Development of patient-specific biomechanical models for predicting large breast deformation. Physics in medicine and biology. 2012;57(2):455-72. doi: 10.1088/0031-9155/57/2/455. PubMed PMID: WOS:000299169200012.

Hasse, K. et al., 2016, Medical Physics, 43(3):1299-311.

He J, Yang Y, Wang Y, Zeng D, Bian Z, Zhang H, Sun J, Xu Z, Ma J. Optimizing a Parameterized Plug-and-Play ADMM for Iterative Low-Dose CT Reconstruction. IEEE Trans Med Imaging. 2019;38(2):371-82. doi: 10.1109/TMI.2018.2865202. PubMed PMID: 30106717.

Hickey BE, Lehman M, Francis DP, See AM. Partial breast irradiation for early breast cancer. Cochrane Db Syst Rev. 2016(7). doi: Artn Cd007077 10.1002/14651858.Cd007077.Pub3. PubMed PMID: WOS:000391289400017.

Hoekstra N, Fleury E, Merino Lara TR, van der Baan P, Bahnerth A, Struik G, Hoogeman M, Pignol JP. Long-term risks of secondary cancer for various whole and partial breast irradiation techniques. Radiotherapy and oncology : journal of the European Society for Therapeutic Radiology and Oncology. 2018;128(3):428-33. doi: 10.1016/j.radonc.2018.05.032. PubMed PMID: 29914648.

Holbrook M, Clark DP, Badea CT. Low-dose 4D cardiac imaging in small animals using dual source micro-CT. Physics in medicine and biology. 2018;63(2):025009. doi: 10.1088/1361-6560/aa9b45. PubMed PMID: 29148430; PubMed Central PMCID: PMC5831335.

Holland R, Veling SH, Mravunac M, Hendriks JH. Histologic multifocality of Tis, T1-2 breast carcinomas. Implications for clinical trials of breast-conserving surgery. Cancer. 1985;56(5):979-90. PubMed PMID: 2990668.

Horton JK, Blitzblau RC, Yoo S, Geradts J, Chang Z, Baker JA, Georgiade GS, Chen W, Siamakpour-Reihani S, Wang C, Broadwater G, Groth J, Palta M, Dewhirst M, Barry WT, Duffy EA, Chi JT, Hwang ES. Preoperative Single-Fraction Partial Breast Radiation Therapy: A Novel Phase 1, Dose-Escalation Protocol With Radiation Response Biomarkers. International journal of radiation oncology, biology, physics. 2015;92(4):846-55. doi: 10.1016/j.ijrobp.2015.03.007. PubMed PMID: 26104938; PubMed Central PMCID: PMC4481883.

International Search Report and Written Opinion issued in App. No. PCT/US2021/016233, mailing date Apr. 21, 2021, 10 pages.

Jagsi R, Ben-David MA, Moran JM, Marsh RB, Griffith KA, Hayman JA, Pierce LJ. Unacceptable cosmesis in a protocol investigating intensity-modulated radiotherapy with active breathing control for accelerated partial-breast irradiation. International journal of radiation oncology, biology, physics. 2010;76(1):71-8. doi: 10.1016/j.ijrobp.2009.01.041. PubMed PMID: 19409733; PubMed Central PMCID: PMC4414125.

Jin, J. et al., 2016, International journal of radiation oncology, biology, physics, 95(3):1058-66.

Johansson S, Svensson H, Denekamp J. Dose response and latency for radiation-induced fibrosis, edema, and neuropathy in breast cancer patients. International journal of radiation oncology, biology, physics. 2002;52(5):1207-19. PubMed PMID: 11955731.

Jozsef G, DeWyngaert JK, Becker SJ, Lymberis S, Formenti SC. Prospective study of cone-beam computed tomography image-guided radiotherapy for prone accelerated partial breast irradiation. International journal of radiation oncology, biology, physics. 2011;81(2):568-74. doi: 10.1016/j.ijrobp.2010.11.029. PubMed PMID: 21570210.

Jun CH, Decker R, Stoianovici D. Using optical tracking for kinematic testing of medical robots. Int J Med Robot Comp. 2018;14(2). doi: Artn E1890 10.1002/Rcs.1890. PubMed PMID: WOS:000426656700009.

Kalender, W.A. et al., 2012, European radiology, 22(1): 1-8).

Kang E, Chang W, Yoo J, Ye JC. Deep Convolutional Framelet Denosing for Low-Dose CT via Wavelet Residual Network. IEEE Trans Med Imaging. 2018;37(6):1358-69. doi: 10.1109/TMI.2018. 2823756. PubMed PMID: 29870365.

Kang E, Koo HJ, Yang DH, Seo JB, Ye JC. Cycle-consistent adversarial denoising network for multiphase coronary CT angiography. Medical physics. 2019;46(2):550-62. doi: 10.1002/mp.13284. PubMed PMID: 30449055.

Kang, D. et al., 2013, Medical Imaging: Image processing, 8669.

Keller LM, Sopka DM, Li T, Klayton T, Li J, Anderson PR, Bleicher RJ, Sigurdson ER, Freedman GM. Five-year results of whole breast intensity modulated radiation therapy for the treatment of early stage breast cancer: the Fox Chase Cancer Center experience. International journal of radiation oncology, biology, physics. 2012;84(4):881-7. doi: 10.1016/j.ijrobp.2012.01.069. PubMed PMID: 22909414.

Kelly A, Hardcastle N, Metcalfe P, Cutajar D, Quinn A, Foo K, Cardoso M, Barlin S, Rosenfeld A. Surface dosimetry for breast radiotherapy in the presence of immobilization cast material. Physics in medicine and biology. 2011;56(4):1001-13. doi: 10.1088/0031-9155/56/4/008. PubMed PMID: 21258139.

Keyrilainen, J. et al., 2008, Radiology, 249(1):321-7.

Kim DW, Chung WK, Yoon M. Imaging doses and secondary cancer risk from kilovoltage cone-beam CT in radiation therapy. Health physics. 2013;104(5):499-503. doi: 10.1097/HP.0b013e318285c685. PubMed PMID: 23532078.

Kingma, D. et al., 2014, arXiv:14126980.

Kirby AM, Evans PM, Donovan EM, Convery HM, Haviland JS, Yarnold JR. Prone versus supine positioning for whole and partial-breast radiotherapy: a comparison of non-target tissue dosimetry. Radiotherapy and oncology : journal of the European Society for Therapeutic Radiology and Oncology. 2010;96(2):178-84. doi: 10.1016/j.radonc.2010.05.014. PubMed PMID: 20561695.

Kirby, A.M. et al., 2011, Radiotherapy and oncology: journal of the European Society for Therapeutic Radiology and Oncology, 100(2):221-6.

Kirwan, L., Aesthetic surgery journal, 20 22(4):355-63.

Kishan AU, Wang PC, Sharif J, Kupelian PA, Steinberg ML, McCloskey SA. Clinical Indicators of Psychosocial Distress Predict for Acute Radiation-Induced Fatigue in Patients Receiving Adjuvant Radiation Therapy for Breast Cancer: An Analysis of Patient-Reported Outcomes. International journal of radiation oncology, biology, physics. 2016;95(3):946-55. doi: 10.1016/j.ijrobp.2016.01. 062. PubMed PMID: 27105720.

Koning Health. (Feb. 4, 2015). FDA Approves 3D-Koning Breast CT. koninghealth.com/en/fda-approves-3d-koning-breast-ct.

Krauss DJ, Kestin LL, Mitchell C, Martinez AA, Vicini FA. Changes in temporal patterns of local failure after breast-conserving therapy and their prognostic implications. Int J Radiat Oncol. 2004;60(3):731-40. doi: 10.1016/j.ijrobp.2004.04.010. PubMed PMID: WOS:000224350900005.

Krengli M, Masini L, Caltavuturo T, Pisani C, Apicella G, Negri E, Deantonio L, Brambilla M, Gambaro G. Prone versus supine position for adjuvant breast radiotherapy: a prospective study in patients with pendulous breasts. Radiation oncology. 2013;8:232. doi: 10.1186/1748-717X-8-232. PubMed PMID: 24103708; PubMed Central PMCID: PMC3852328.

Lakosi F, Gulyban A, Janvary L, Simoni SB, Jansen N, Seidel L, Kovacs A, Vavassis P, Coucke P. Respiratory Motion, Anterior Heart Displacement and Heart Dosimetry: Comparison Between Prone (Pr) and Supine (Su) Whole Breast Irradiation. Pathology oncology research : POR. 2015;21(4):1051-8. doi: 10.1007/s12253-015-9932-9. PubMed PMID: 25840562.

Lebrun, M. 2012, Image Process Line, 2:175-213.

Lee, A., Rajagopal, V., Chung, J. H., Bier, P., Nielsen, P. M., & Nash, M. P. (Mar. 2008). Biomechanical modelling for breast image registration. In Medical Imaging 2008: Visualization, Image-Guided Procedures, and Modeling (vol. 6918, pp. 299-306). SPIE.

(56) References Cited

OTHER PUBLICATIONS

Li S, Zeng D, Peng J, Bian Z, Zhang H, Xie Q, Wang Y, Liao Y, Zhang S, Huang J, Meng D, Xu Z, Ma J. An Efficient Iterative Cerebral Perfusion CT Reconstruction via Low-Rank Tensor Decomposition With Spatial-Temporal Total Variation Regularization. IEEE Trans Med Imaging. 2019;38(2):360-70. doi: 10.1109/TMI.2018.2865198. PubMed PMID: 30106716.

Li Y, Zhang X, Yeung KW. A 3D biomechanical model for numerical simulation of dynamic mechanical interactions of bra and breast during wear. Sen-I Gakkaishi. 2003;59(1):12-21. PubMed PMID: WOS:000181416600008.

Lindfors KK, Boone JM, Nelson TR, Yang K, Kwan AL, Miller DF. Dedicated breast CT: initial clinical experience. Radiology. 2008;246(3):725-33. doi: 10.1148/radiol.2463070410. PubMed PMID: 18195383; PubMed Central PMCID: PMC2798097.

Liu F, Klein E. Biomechanical Modeling of Compressed Breast Tissue. Medical physics. 2018;45(6):E228-E9. PubMed PMID: WOS:000434978001059.

Lyu Q, Yu VY, Ruan D, Neph R, O'Connor D, Sheng K. A novel optimization framework for VMAT with dynamic gantry couch rotation. Physics in medicine and biology. 2018;63(12):125013. doi: 10.1088/1361-6560/aac704. PubMed PMID: 29786614; PubMed Central PMCID: PMC6075870.

Lyu, Q. et al., 2018, Medical Physics, 45(6):2603-10.

Lyu, Q. et al., 2019, Iterative reconstruction for low dose CT using Plug-and-Play alternating direction method of multipliers (ADMM) framework, SPIE Medical Imaging : Image Processing, 10949. https://doi.org/10.1117/12.2512484.

M. Z. et al., 2017, IEEE/ASME Transactions on Mechatronics, 22(1):91-8.

Martinez, R.V. et al., 2013, Advanced Materials, 25(2):205-12.

Mechlem K, Ehn S, Sellerer T, Braig E, Munzel D, Pfeiffer F, Noel PB. Joint Statistical Iterative Material Image Reconstruction for Spectral Computed Tomography Using a Semi-Empirical Forward Model. IEEE Trans Med Imaging. 2018;37(1):68-80. doi: 10.1109/TMI.2017.2726687. PubMed PMID: 28715327.

Mira A, Payan Y, Carton AK, de Carvalho PM, Li ZJ, Devauges V, Muller S. Simulation of breast compression using a new biomechanical model. Pro Biomed Opt Imag. 2018;10573. doi: Unsp 105735a 10.1117/12.2293488. PubMed PMID: WOS:000436173700181.

Morrow NV, Stepaniak C, White J, Wilson JF, Li XA. Intra- and interfractional variations for prone breast irradiation: an indication for image-guided radiotherapy. International journal of radiation oncology, biology, physics. 2007;69(3):910-7. doi: 10.1016/j.ijrobp.2007.06.056. PubMed PMID: 17889272.

Mukesh MB, Harris E, Collette S, Coles CE, Bartelink H, Wilkinson J, Evans PM, Graham P, Haviland J, Poortmans P, Yarnold J, Jena R. Normal tissue complication probability (NTCP) parameters for breast fibrosis: pooled results from two randomised trials. Radiotherapy and oncology : journal of the European Society for Therapeutic Radiology and Oncology. 2013;108(2):293-8. doi: 10.1016/j.radonc.2013.07.006. PubMed PMID: 23953408.

Mulliez T, Gulyban A, Vercauteren T, van Greveling A, Speleers B, De Neve W, Veldeman L. Setup accuracy for prone and supine whole breast irradiation. Strahlentherapie und Onkologie : Organ der Deutschen Rontgengesellschaft [et al]. 2016;192(4):254-9. doi: 10.1007/s00066-016-0943-6. PubMed PMID: 26864048.

O'Connell AM, Karellas A, Vedantham S. The potential role of dedicated 3D breast CT as a diagnostic tool: review and early clinical examples. The breast journal. 2014;20(6):592-605. doi: 10.1111/tbj.12327. PubMed PMID: 25199995; PubMed Central PMCID: PMC4201870.

O'Connell A. et al., AJR American journal of roentgenology, 195(2):496-509).

Obayomi-Davies O, Kole TP, Oppong B, Rudra S, Makariou EV, Campbell LD, Anjum HM, Collins SP, Unger K, Willey S, Tousimis E, Collins BT. Stereotactic Accelerated Partial Breast Irradiation for Early-Stage Breast Cancer: Rationale, Feasibility, and Early Experience Using the CyberKnife Radiosurgery Delivery Platform. Frontiers in oncology. 2016;6:129. doi: 10.3389/fonc.2016.00129. PubMed PMID: 27242967; PubMed Central PMCID: PMC4876543.

Olivotto IA, Whelan TJ, Parpia S, Kim DH, Berrang T, Truong PT, Kong I, Cochrane B, Nichol A, Roy I, Germain I, Akra M, Reed M, Fyles A, Trotter T, Perera F, Beckham W, Levine MN, Julian JA. Interim cosmetic and toxicity results from RAPID: a randomized trial of accelerated partial breast irradiation using three-dimensional conformal external beam radiation therapy. Journal of clinical oncology : official journal of the American Society of Clinical Oncology. 2013;31(32):4038-45. doi: 10.1200/JCO.2013.50.5511. PubMed PMID: 23835717.

Rahimi A, Thomas K, Spangler A, Rao R, Leitch M, Wooldridge R, Rivers A, Seiler S, Albuquerque K, Stevenson S, Goudreau S, Garwood D, Haley B, Euhus D, Heinzerling J, Ding C, Gao A, Ahn C, Timmerman R. Preliminary Results of a Phase 1 Dose-Escalation Trial for Early-Stage Breast Cancer Using 5-Fraction Stereotactic Body Radiation Therapy for Partial-Breast Irradiation. International journal of radiation oncology, biology, physics. 2017;98(1):196-205e2. doi: 10.1016/j.ijrobp.2017.01.020. PubMed PMID: 28586960.

Rahimi A, Timmerman R. New Techniques for Irradiating Early Stage Breast Cancer: Stereotactic Partial Breast Irradiation. Seminars in radiation oncology. 2017;27(3):279-88. doi: 10.1016/j.semradonc.2017.02.007. PubMed PMID: 28577835.

Rajagopal V, Chung JH, Highnam RP, Warren R, Nielsen PMF, Nash MP. Mapping Microcalcifications Between 2D Mammograms and 3D MRI Using a Biomechanical Model of the Breast. Computational Biomechanics for Medicine. 2010:17-+. doi: 10.1007/978-1-4419-5874-7_3. PubMed PMID: WOS:000283101400003.

Rajagopal V, Lee A, Chung JH, Warren R, Highnam RP, Nielsen PMF, Nash MP. Towards tracking breast cancer across medical images using subject-specific biomechanical models. Medical Image Computing and Computer-Assisted Intervention—Miccai 2007, Pt 1, Proceedings. 2007;4791:651-8. PubMed PMID: WOS:000250916000079.

Ratosa I, Jenko A, Oblak I. Breast size impact on adjuvant radiotherapy adverse effects and dose parameters in treatment planning. Radiology and oncology. 2018;52(3):233-44. doi: 10.2478/raon-2018-0026. PubMed PMID: 30210048; PubMed Central PMCID: PMC6137355.

Rault E, Lacornerie T, Dang HP, Crop F, Lartigau E, Reynaert N, Pasquier D. Accelerated partial breast irradiation using robotic radiotherapy: a dosimetric comparison with tomotherapy and three-dimensional conformal radiotherapy. Radiation oncology. 2016;11:29. doi: 10.1186/s13014-016-0607-9. PubMed PMID: 26919837; PubMed Central PMCID: PMC4769549.

Rose S, Andersen MS, Sidky EY, Pan X. Noise properties of CT images reconstructed by use of constrained total-variation, data-discrepancy minimization. Medical physics. 2015;42(5):2690-8. doi: 10.1118/1.4914148. PubMed PMID: 25979067; PubMed Central PMCID: PMC4425727.

Russo AL, Taghian AG. Fat necrosis of the breast in the accelerated partial breast irradiation era: the need for a universal grading system. Breast cancer research and treatment. 2013;140(1):1-11. doi: 10.1007/s10549-013-2611-1. PubMed PMID: 23797180.

Samani A, Bishop J, Yaffe MJ, Plewes DB. Biomechanical 3-D finite element modeling of the human breast using MRI data. Ieee T Med Imaging. 2001;20(4):271-9. doi: Doi 10.1109/42.921476. PubMed PMID: WOS:000168621500002.

Sechopoulos I. X-ray scatter correction method for dedicated breast computed tomography. Medical physics. 2012;39(5):2896-903. doi: 10.1118/1.4711749. PubMed PMID: 22559662; PubMed Central PMCID: PMC3356324.

Sechopoulos, I., 2012, Medical Physics, 39(5):2896-903.

Sheng K, Gou S, Wu J, Qi SX. Denoised and texture enhanced MVCT to improve soft tissue conspicuity. Medical physics. 2014;41(10):101916. doi: 10.1118/1.4894714. PubMed PMID: 25281968.

Sheng, K. et al., 2014, Medical Physics, 41(10):101916.

Shepherd RF, Ilievski F, Choi W, Morin SA, Stokes AA, Mazzeo AD, Chen X, Wang M, Whitesides GM. Multigait soft robot. Proceedings of the National Academy of Sciences of the United

(56) References Cited

OTHER PUBLICATIONS

States of America. 2011;108(51):20400-3. doi: 10.1073/pnas. 1116564108. PubMed PMID: 22123978; PubMed Central PMCID: PMC3251082.

Smith TE, Lee D, Turner BC, Carter D, Haffty BG. True recurrence vs. new primary ipsilateral breast tumor relapse: An analysis of clinical and pathologic differences and their implications in natural history, prognoses, and therapeutic management. Int J Radiat Oncol. 2000;48(5):1281-9. doi: Doi 10.1016/S0360-3016(00)01378-X. PubMed PMID: WOS:000165604600002.

Sreehari, S. et al., 2016, IEEE T Comput. Imag., 2(4):408-23.

Stegman LD, Beal KP, Hunt MA, Fornier MN, McCormick B. Long-term clinical outcomes of whole-breast irradiation delivered in the prone position. International journal of radiation oncology, biology, physics. 2007;68(1):73-81. doi: 10.1016/j.ijrobp.2006.11.054. PubMed PMID: 17337131.

Strom EA, Amos RA, Shaitelman SF, Kerr MD, Hoffman KE, Smith BD, Tereffe W, Stauder MC, Perkins GH, Amin MD, Wang X, Poenisch F, Ovalle V, Buchholz TA, Babiera G, Woodward WA. Proton partial breast irradiation in the supine position: Treatment description and reproducibility of a multibeam technique. Practical radiation oncology. 2015;5(4):e283-90. doi: 10.1016/j.prro.2015.01.010. PubMed PMID: 25804105.

Strydhorst JH, Caudrelier JM, Clark BG, Montgomery LA, Fox G, MacPherson MS. Evaluation of a thermoplastic immobilization system for breast and chest wall radiation therapy. Medical dosimetry : official journal of the American Association of Medical Dosimetrists. 2011;36(1):81-4. doi: 10.1016/j.meddos.2010.01.001. PubMed PMID: 20346646.

Tanner C, Degenhard A, Schnabel JA, Castellano-Smith AD, Hayes C, Sonoda LI, Leach MO, Hose DR, Hill DLG, Hawkes DJ. Comparison of biomechanical breast models: a case study. Medical Imaging 2002: Image Processing, vol. 1-3. 2002;4684:1807-18. doi: Doi 10.1117/12.467155. PubMed PMID: WOS:000177471900194.

\* cited by examiner

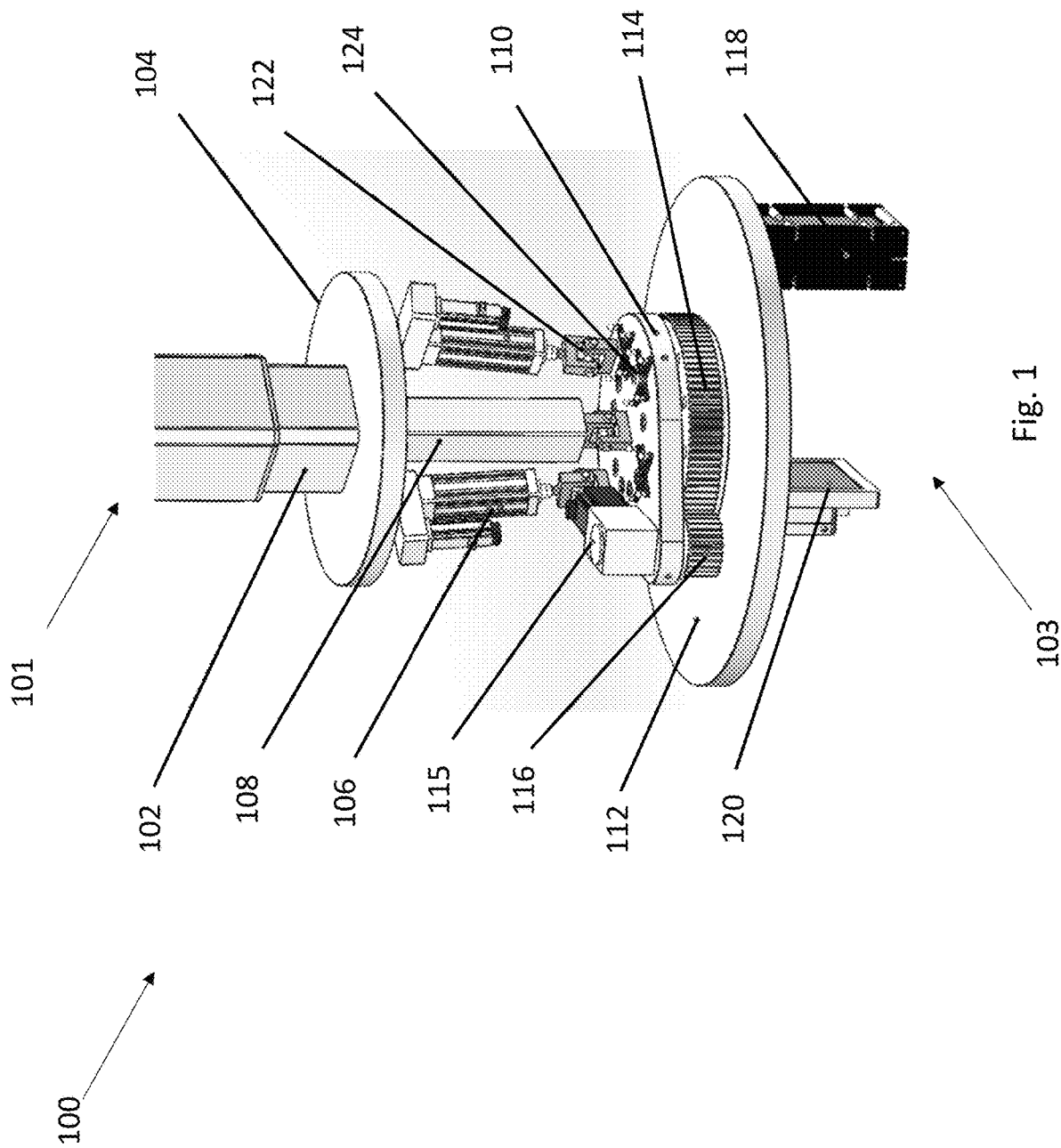

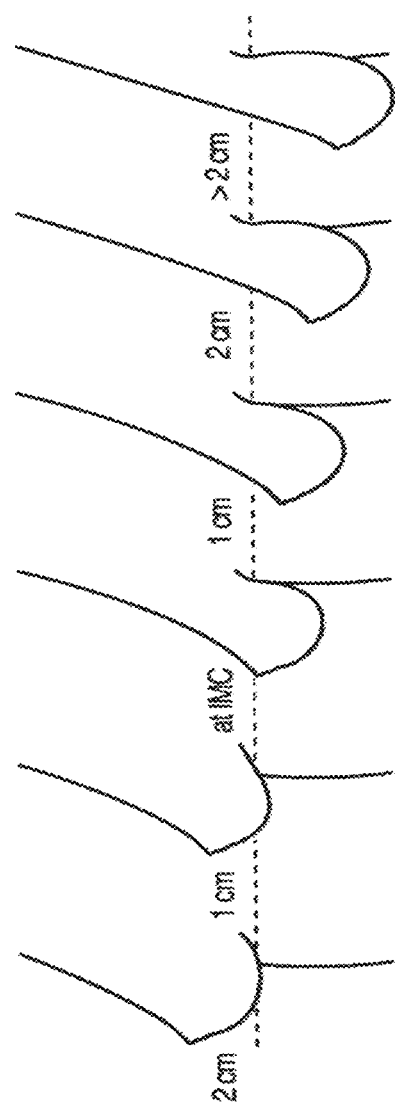
Fig. 6A
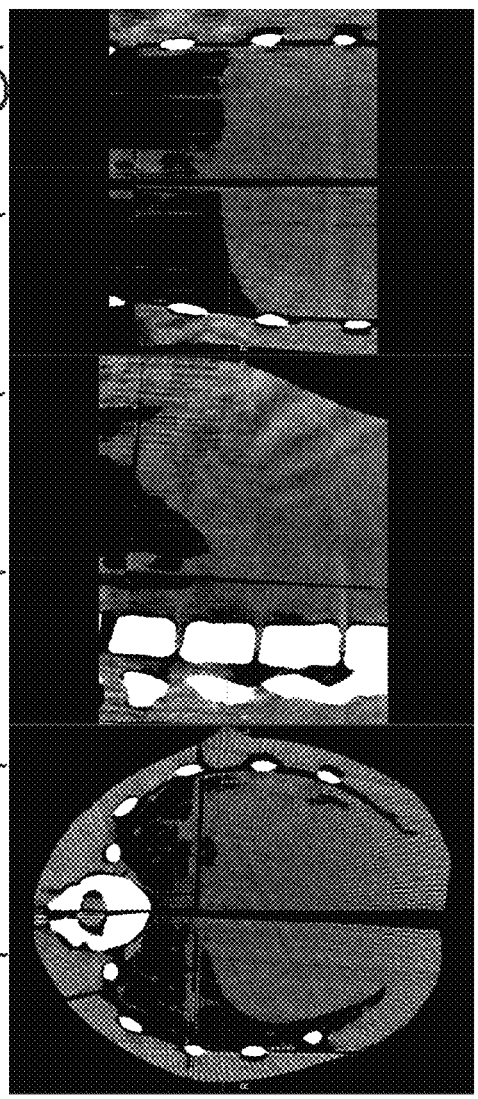
Fig. 6B
Fig. 6A- Fig. 6B

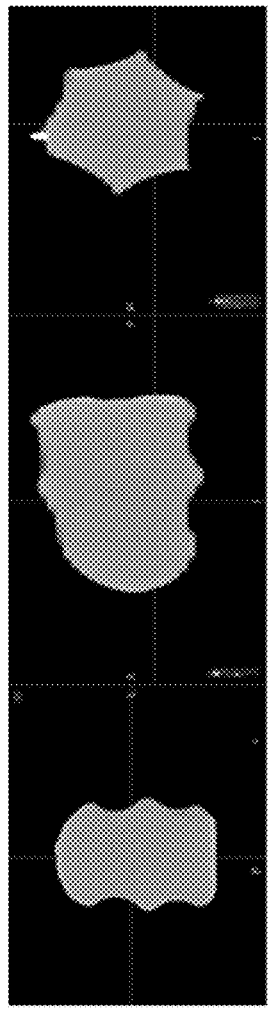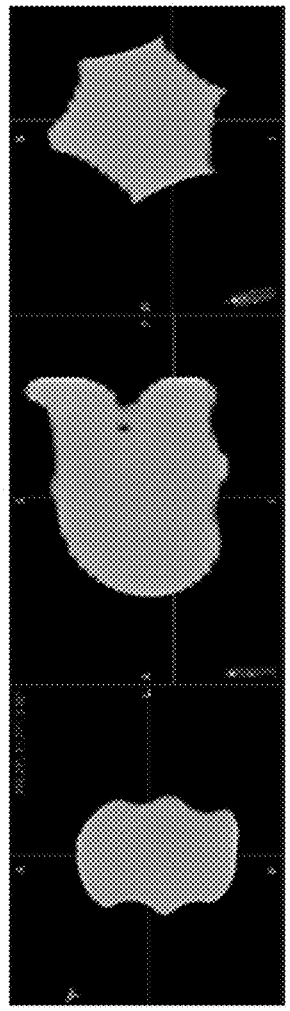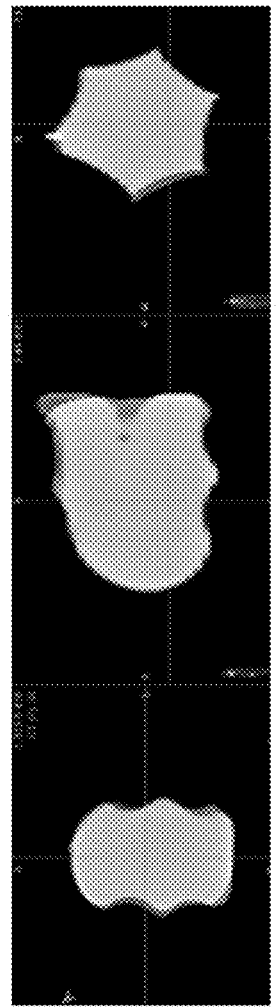
Fig. 8A  Fig. 8B  Fig. 8C
Fig. 8A- Fig. 8C

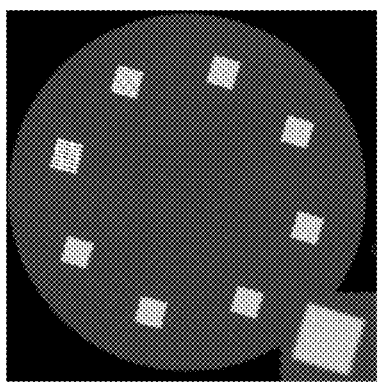
Fig. 10D
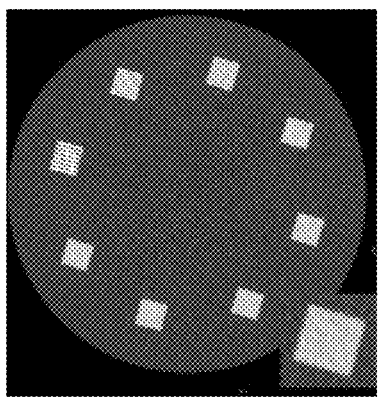
Fig. 10C
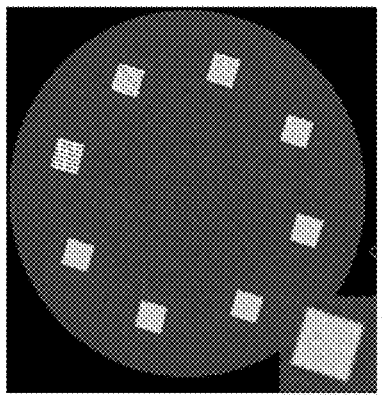
Fig. 10B
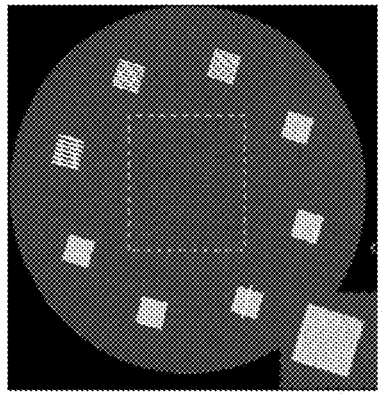
Fig. 10A
Fig. 10A- Fig. 10D

SUPINE BREAST CT SCANNER

CROSS-REFERENCE TO RELATED APPLICATIONS

This application is a 35 U.S.C. § 371 national phase application from, and claiming priority to, International Application No. PCT/US2021/16233, filed Feb. 2, 2021, which claims priority to U.S. Provisional Patent Application No. 62/969,402, filed on Feb. 3, 2020, both of which are incorporated herein by reference in their entirety.

BACKGROUND OF THE INVENTION

Mammography has been the "gold standard" for early stage breast cancer detection and instrumental in reducing the mortality rate due to breast cancer. On the other hand, being a 2D image, mammography is not ideal to differentiate overlapping tissues in the projection direction. This limitation is particularly severe for patients with dense breast tissues. The compression required for mammography can be hard to tolerate to some patients, reducing the compliance for such an exam. The mammography breast geometry is also different from the radiotherapy treatment geometry, making it useless for image-guided radiotherapy. Although whole-body CT can provide 3D breast images, it is an extremely inefficient use of radiation dose. The resolution of the whole-body CT scanner is also substantially worse than that of mammography due to the large field-of-view. Whole body cone beam CT (CBCT) further suffers from severe artifacts due to beam hardening, photon starvation, and scattering. Dedicated breast CT was then developed to answer to the needs to improve the visualization and disease detection in 3D geometry while avoiding unnecessary imaging dose to the patient body. Currently, dedicated breast CT is performed mostly in the prone position and less frequently in the upright position to take advantage of the breast separation from the chest wall. However, there is a substantial difference in the breast morphology between different patient postures. It is difficult to use the prone image information for supine treatment, which is the predominant position in radiotherapy and surgery. There is not a dedicated supine breast CT due to the lack of viable setup and immobilization devices in this position.

Thus, there is a need in the art for a more effective method to distance the breast from the chest wall and then image the breast in the supine position. The present invention meets this need.

SUMMARY OF THE INVENTION

In one aspect, the present invention relates to a cone beam CT scanner comprising: a receiving section configured to receive a breast of the subject whilst in the supine position; a radiation imaging section comprising an x-ray tube and a detector which face each other and have the receiving section interposed therebetween; and a drive unit operable to move the receiving section to a position above the breast of the supine subject, suitable for imaging the breast of the subject. In one embodiment, the receiving section comprises: a lifting column securely attached to the ceiling at a proximal end and perpendicularly attached to top surface of a fixed base at a distal end and is provided with a telescopic mechanism, configured to extend a few inches or several feet; a moving platform spaced apart from the fixed base in a downward direction by at least two cylinders and a fixed link, wherein each of the cylinders is hingedly connected to the moving platform and provided with a telescoping mechanism, capable of extending the length at least a few inches at a distal end and thereby capable to tilt the moving platform upward and downward; and a mounting base spaced apart from the moving platform by a slew bearing in a downward direction, wherein rotation of the slew bearing via a driving gear, causes the mounting base to rotate around a vertical axis. In one embodiment, the CT scanner further comprises a cover configured to envelop the scanner. In one embodiment, the cover further comprises a head notch, configured for positioning a head of the subject. In one embodiment, the CT scanner further comprises a tracking system. In one embodiment, the tracking system is selected from the group consisting of: a stereoscopic optical tracker, a stereoscopic video-based tracker, an electromagnetic tracker, a mechanical link-based tracker, a structured-light or laser-based surface scanner, or combinations thereof. In one embodiment, the tracking system comprises at least one passive marker, a control unit and at least one camera. In one embodiment, the x-ray tube is a rotating anode pulsed x-ray source. In one embodiment, the detector is a flat panel detector.

In one aspect, the present invention relates to a method for breast radiography using a cone beam CT (CBCT) scanner, comprising: providing a patient table, configured for a subject in a supine position; providing a breast fixation device to stabilize a subject's breast during imaging; providing a cone beam CT scanner, comprising a receiving section, a radiation section comprising an x-ray tube and a detector which face each other and have the receiving section interposed therebetween and a drive unit; operating the drive unit to position the scanner at a predetermined position and orientation; and obtaining an image of the subject. In one embodiment, the method further comprising the step of extending a telescopic mechanism of the drive unit toward the subject. In one embodiment, the telescopic mechanism comprises a lifting column. In one embodiment, the method further comprising changing the position or orientation of the scanner. In one embodiment, wherein the angle of the scanner relative to the patient table is changed by at least 5 degrees. In one embodiment, the method comprising collecting at least 3 images of the subject. In one embodiment, the method comprising creating a three-dimensional representation of a tissue of the subject from the at least 3 images. In one embodiment, the at least 3 images are gathered at a frame rate of between 1 f/s and 50 f/s. In one embodiment, wherein the at least 3 images are gathered at a frame rate of between 25 f/s and 35 f/s. In one embodiment, wherein the scanner comprises a notch to accommodate a head of the subject, and further comprising positioning the notch about the head of the subject. In one embodiment, the method further comprising calculating a position and orientation of the scanner relative to the patient table. In one embodiment, the method further comprising obtaining laser sample data. In one embodiment, further comprising calculating an absolute position of an area of interest within a tissue of the subject. In one embodiment, the method further comprising applying a treatment to the area of interest using a separate instrument.

BRIEF DESCRIPTION OF THE DRAWINGS

The following detailed description of embodiments of the invention will be better understood when read in conjunction with the appended drawings. It should be understood, how- FIG. 1 depicts a side view of an exemplary supine breast CT.

FIG. 2A depicts a perspective view of the supine CT. FIG. 2B depicts a close up view of the optical localizers.

FIG. 5A depicts a breast phantom in its natural supine position. FIG. 5B depicts the same breast phantom being immobilized by the prototypical soft robot. FIG. 5C depicts axial slices of a breast phantom in its natural supine position. FIG. 5D depicts axial slices of the same breast phantom being immobilized by the prototypical soft robot.

FIG. 6A through FIG. 6B depicts stages of fabricating a non-human primate phantom for dosimetry purposes with realistic bone, elastic muscles and other soft tissues. FIG. 6A depicts the varying ptosis stage. FIG. 6B depicts the 3D printed non-human primate (NHP) phantom for preclinical dosimetry with bones and various types of soft tissues.

FIG. 8A through FIG. 8C depicts repeatability of BSSR breast set up. FIG. 8A and FIG. 8B depicts two separate applications of BSSR and CT scans. FIG. 8C depicts the superimposed images. Columns show axial, sagittal and coronal images, respectively.

FIG. 10A through FIG. 10D depicts reconstructed image with zoomed in ROI (red square) of the ACR phantom. FIG. 10A depicts the reconstructed image using Plug-and-Play ADMM. FIG. 10B depicts the reconstructed image using TV. FIG. 10C depicts the reconstructed image using FBP from low dose (5%) CT data. FIG. 10D depicts reconstructed image using FBP from standard dose CT data.

FIG. 11A depicts the reconstructed image using LD-FBP. FIG. 11B depicts the reconstructed images using LD-FBP-ConvNet. FIG. 11C depicts the reconstructed image using LD-PnP-ConvNet. FIG. 11D depicts the reconstructed image using LD-TV.

DETAILED DESCRIPTION

Figure 2B:
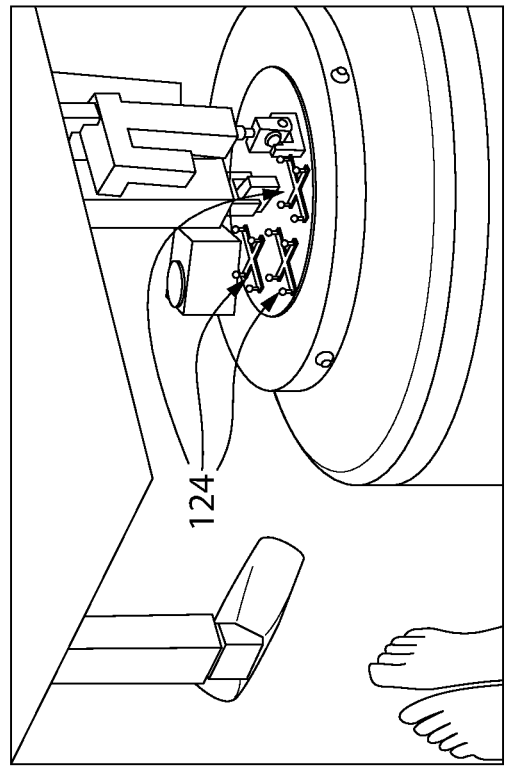
FIG. 2A through FIG. 2B depicts an exemplary CAD rendering of the supine CT to show its key components.

It is to be understood that the figures and descriptions of the present invention have been simplified to illustrate elements that are relevant for a clear understanding of the present invention, while eliminating, for the purpose of clarity, many other elements found in the field of imaging devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, exemplary materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

The terms "patient," "subject," "individual," and the like are used interchangeably herein, and refer to any animal amenable to the systems, devices, and methods described herein. The patient, subject or individual may be a mammal, and in some instances, a human.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Supine Cone Beam CT Scan (CBCT)

The present invention relates in part to a ceiling mounted CBCT to accommodate varying patient size and tissue surface morphology. The supine cone beam CT scanner is able to take images in a supine position from tissues such as breast that have unique biomechanical properties.

Referring now to FIG. 1, an exemplary supine CT scanner 100 is shown. Scanner 100 comprises a proximal end 101, a distal end 103, a vertical lifting column 102, a fixed base 104, a plurality of cylinders 106, a fixed link 108, a moving platform 110, a mounting base 112, slew bearing 114, driving gear 116, X-ray tube 118, flat panel detector 120.

Lifting column 102 is securely attached to the ceiling at proximal end 101 and perpendicularly attached to top surface of fixed base 104 at distal end 103. In one embodiment, lifting column 102 is provided with a telescopic mechanism, capable of extending a few inches at several feet at distal end 103. In one embodiment, lifting column 102 is able to support heavy loads of at least about 1000 N. In one embodiment, lifting column 102 is able to support heavy loads of at least about 3000 N. In one embodiment, lifting column 102 is able to support heavy loads of at least about 5000 N. In one embodiment, lifting column 102 is able to support heavy loads of at least about 6000 N. In one embodiment, lifting column 102 is hydraulically driven and can respond to human force guidance. In one embodiment, lifting column 102 is driven by a control unit.

Fixed base 104 is spaced apart from moving platform 110 in a downward direction. Fixed base 104 has a bottom surface confronting the upper surface of moving platform 110 and at least two cylinders 106 that are disposed on the lower surface and are angularly displaced from one another about a central line which extends in the downward direction.

The at least two cylinders 106 define first and second lengths respectively, in the downward direction. Each of the cylinders 106 is provided with a telescoping mechanism, capable of extending the length at least a few inches at distal end 103. In some embodiments, each of the cylinders 106 is capable of extending the length in a range between one inch and 20 inches. Each of the cylinders 106 is connected to upper surface of moving platform 110 through first hinge 122, as to permit free rotation of moving platform 110 relative to the at least two cylinders 106. In one embodiment, first hinge 122 can be Hooke hinges, barrel hinges, piano hinges, flush hinges, pivot hinges, flush hinges, or any other suitable hinge. In one embodiment, the at least two cylinders 102 can be satellite roller screws or any other suitable cylinders capable of extending their length.

Fixed base 104 is further connected to moving platform 110 through a fixed link 108. Fixed link 108 is perpendicularly attached to bottom surface of fixed base 104 and hingedly connected to upper surface of moving platform 110 at distal end 103. Fixed link 108 is a supporting column to support the heavy load. In one embodiment, fixed link 108 can be selected from the group consisting of: a sphere, a cone, a pyramid, a cylinder, a tube, a ring, a tetrahedron, a hexagon, an octagon, or any irregular shapes. In one embodiment, the length of fixed link 108 can be between 5 and 20 inches.

In one embodiment, when one of cylinders 106 is driven to be extended and the other cylinders 106 are driven to be retracted, moving platform 110 can be tilted upward and downward relative to fixed base 104. In some embodiments, the cylinders 106 may be configured to tilt moving platform 110 to an angle relative to fixed base 104 in a range from −30 degrees to +30 degrees.

Scanner 100 further comprises a tracking system. The tracking system may be, for example, but not limited to, a stereoscopic optical tracker (e.g., infrared or visible light based), a stereoscopic video-based tracker, an electromagnetic tracker, a mechanical link-based tracker, a structured-light or laser-based surface scanner, or a combination thereof. A tracking system may further comprise at least one passive marker 124, a control unit and at least one camera 128 (FIG. 2A) positioned such that at least one passive marker is within its field of view. In one embodiment, at least one passive marker 124 is rigidly attached to the top surface of moving platform 110. In one embodiment, three passive markers can be used to increase measurement precision. With the use of this marker geometry, an optical, stereoscopic tracking system or navigation system can unambiguously determine the position in space of scanner 100 relative to the patient.

In one embodiment, camera 128 is placed on the ceiling, wall, or other support structure with its pointing angle adjusted to cover the working volume of interest. In one embodiment, a single camera 128 can be used. In one embodiment, the number of cameras 128 employed in this exemplary system can exceed one to increase the field of view. In one embodiment, scanner 100 may comprise at least 2, 3, 4, 5, or more cameras 128.

Camera 128 can be used for breath-hold imaging. Even if the patient's body maintains the same position as that assumed during the 3D imaging method, locations within the patient's body can move with variations in the patient's physiological activities, such as breathing. Such movement causes a deviation in internal positions within the patient's body from the positions recorded in the image obtained with the 3D imaging method. The tracking of the position and orientation of marker 124 can provide monitoring of physiological activities such as by tracking chest movement or movement of internal structures.

In one embodiment a 3D camera can be used to quantify the surface location, control the hold position, and acquire at least two images at the same breathing position as determined by 3D images.

The control unit may comprise a simulated movement controller to control respective movement of at least two cylinders 106 along the first and second length, thereby permitting moving platform 110 to tilt upward and downward relative to fixed base 104.

In one embodiment, fixed base 104 and moving platform 110 can have any suitable shape, such as substantially quadrilateral, circular or elliptical shape. In one embodiment, fixed base 104 and moving platform 110 can be constructed from any suitable rigid material including but not limited to metal, polymers or combinations thereof. In one embodiment, fixed base 104 and moving platform are made from the same material. In one embodiment, fixed base 104 and moving platform are made from different material. In one embodiment, fixed base 104 has an area larger than that of moving platform 110.

In the depicted embodiment, mounting base 112 is spaced apart from moving platform 110 by slew bearing 114 in a downward direction. A geared servo motor 115 mounted on upper surface of moving platform 110, rotates the slew bearing 114 via a driving gear 116. The rotation of driving gear 116, in either a clockwise or counter clockwise direction, rotates slew bearing 114 and thus, causes mounting base 112 to rotate around the vertical axis.

Mounting base 112 further comprises an X-ray tube 118 and a detector 120 attached perpendicularly to bottom surface of mounting base 112. X-ray tube 118 and detector 120 are spaced apart such that they create a central opening into which an object being imaged is placed. X-ray tube 118 projects a beam of x-ray radiation into the central opening, through the object being imaged and onto detector 120 attached on to the opposite side of mounting base 112. In one embodiment, detector 120 can be a flat panel detector. It will be understood, however, that various detectors and detector arrays can be used in this invention, including any detector configurations used in typical diagnostic fan-beam or cone-beam imaging systems, such as C-arm fluoroscopes, or single-sliced or multi-sliced CT scanners, or mobile and fixed-room fluoroscopy devices which utilize image intensifier technology. In one embodiment, the flat panel detector is provided by CareRay. In one embodiment, detector 120 comprises active areas of different sizes, e.g. different active sizes. According to some embodiments of the present invention, active size of the detectors are tuned to provide a desired level of signal output and/or resolution in defined areas. Optionally, absorbency and/or thickness of detector 120 are additionally tuned to provide a desired output. In one exemplary embodiment, detector 120 comprises an active area of 157.7 mm×157.7 mm. In one exemplary embodiment, detector 120 comprises an active area that can range between 140 mm×140 mm to 170 mm×170 mm. In one embodiment, active area comprises a pixel array of 1024× 1024.

The size (mean diameter) of the pixels of the x-ray detector typically ranges between about 0.1 mm and about 2 mm. Typical geometries of the pixels are rectangular, square, hexagonal, or any other shape that allows for a smart tiling of a one- or two-dimensional area. In one embodiment, pixel size is 154 μm. In one embodiment, detector 120 comprises a frame rate ranging between 1-50 f/s. In one embodiment, detector 120 comprises a frame rate is 30 f/s at full resolution. In one embodiment, the scanning geometry: SID is about 278 mm. In one embodiment, the scanning geometry: SAD is about 203 mm. In one embodiment, the field-of-view is 10 cm or approximately 1.5 liters in cylindrical volume.

In one embodiment, x-ray tube 118 can be a rotating anode pulsed x-ray source. In one embodiment, the time interval between subsequent scans is between 10 milliseconds to 10 minutes. In one embodiment, the time interval between subsequent scans is 2 minutes. It should be understood that the time interval and the scan sweep speed can be determined to meet criteria other than those given by way of example here. For example, the time interval of 2 minutes between sequential samples can be reduced or increased, as needed and desired.

The x-rays received at detector 120 can then be used to produce a two-dimensional or three-dimensional image of the object. In one embodiment, X-ray tube 118 is provided by Toshiba. In one embodiment, x-ray tube 118 comprises a focal spot size of about 0.3-0.4 mm. In one embodiment, the focal spot size is at least 0.1 mm. In one embodiment, the focal spot size is 0.1 mm or less. In one embodiment, x-ray tube 118 comprises a tube voltage ranging about 40-80 kV.

In one embodiment, x-ray tube 118 is mounted in a cooling oil. The oil is circulated through the housing, over x-ray tube 118 and out to a heat exchanger. The present configuration enables the cooling oil to flow directly over the back of the anode target to remove thermal energy. In one embodiment, the oil cooling tank is air cooled.

Mounting base 112 is able to rotate around the vertical axis in a continuous or step-wise manner so that the x-ray beam can be projected through the object, and through a common isocenter, at various angles over a partial or full 360 degree rotation. Detector 120 is rotated around, in coordination with the rotation of x-ray tube 118, so that for each projection angle of the x-ray source, the detector array is positioned opposite the x-ray source on the gantry. The apparatus is thus able to obtain high-quality x-ray images of the targeted object in any projection plane over a partial or full 360 degree rotation.

The positioning of mounting base 112 can be controlled manually or by a motorized system that can be moved electromechanically to a desired position. In one embodiment, a user only has to enter specific desired values for the position of the equipment or for the image to be made, and the control unit automatically controls mounting base 112, so that the equipment take up a favorable configuration, in which x-ray tube 118 and detector 120 attain their required position. In one embodiment, the control unit is furthermore configured to avoid collisions, that is, does not initiate any configurations of mounting base 112 that would cause x-ray tube 118 and detector 120 to collide with the patient.

A computerized motion control system can be attached to motorized components of the scanner 100 and one or more discrete positions and orientations of mounting base 112 may be stored in the computer's memory. During operation of x-ray tube 118, pre-defined positions and orientations may be returned to quickly and easily.

In one embodiment, scanner 100 further comprises laser pointers. In one embodiment, at least one laser pointer is fixed to mounting base 112. In one embodiment, scanner 100 comprises at least four laser pointers fixed to mounting base 112. In one embodiment, laser pointers are placed such that at least one is aimed at at least one wall of the room. In one embodiment, the at least four laser pointers are placed on mounting base 112 to aim at the four walls, where rigid plates are mounted to allow marking. In one embodiment, unique positions are created to represent the typical positions of scanner 100 and their respective laser markers on the wall places are labeled to represent scanner 100 locations relative to the room coordinates. In one embodiment, at least one position is created. In one embodiment, at least 10 positions are created. In one embodiment, at least 50 positions are created. In one embodiment, at least 100 positions are created.

During scanning, laser sample data and scanner 100 position data may be gathered at multiple sample points on one or more walls. In one embodiment, a positioning circuitry may be used to determine scanner 100 position and orientation at each point at which laser sample data is gathered. In one embodiment, laser sample data can be compared with the readings gathered from the tracking system as explained above and used to determine scanner 100 position and orientation.

Figure 2A:
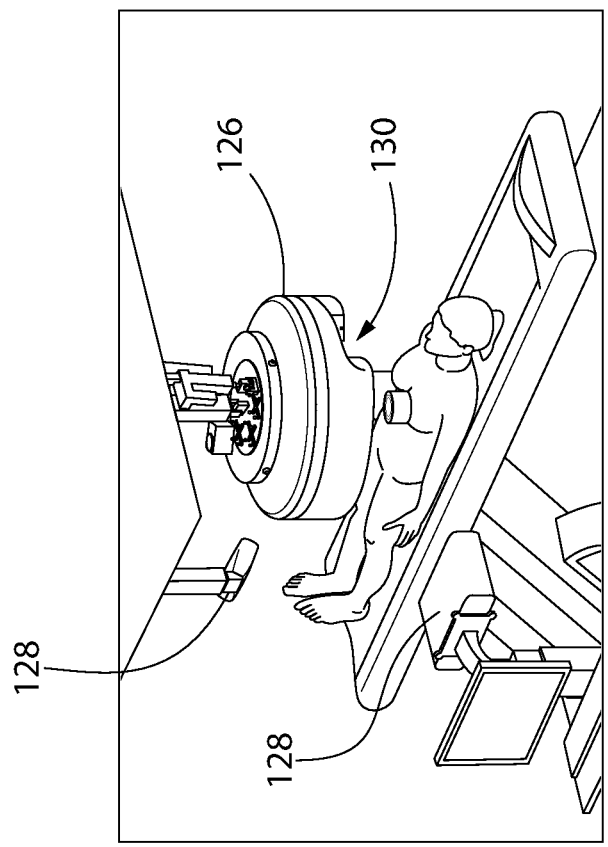

Referring now to FIG. 2A and FIG. 2B, scanner 100, may further comprise a cover 126. Cover 126 envelops scanner 100 and supports the internal structures as described above in a closed housing. Cover 126 further comprises a notch 130 to accommodate the head and to avoid the uncomfortable patient head extension.

Scanner 100 described herein may be advantageously used for two-dimensional and/or three-dimensional x-ray scanning. Individual two-dimensional projections from set angles along the scanner rotation can be viewed, or multiple projections collected throughout a partial or full rotation may be reconstructed using cone or fan beam tomographic reconstruction techniques. In one aspect, the invention could be used for acquiring multi-planar x-ray images in a quasi-simultaneous manner.

Fixation Device

Figure 5A:
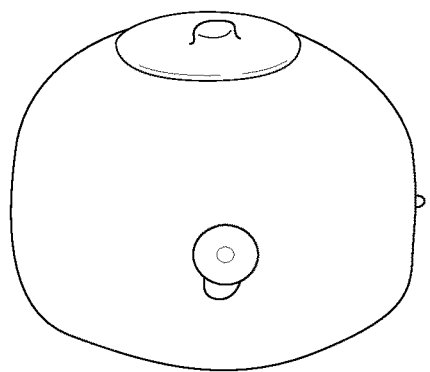
FIG. 5A through FIG. 5D depicts a deformable silicone breast phantom.
Figure 5B:
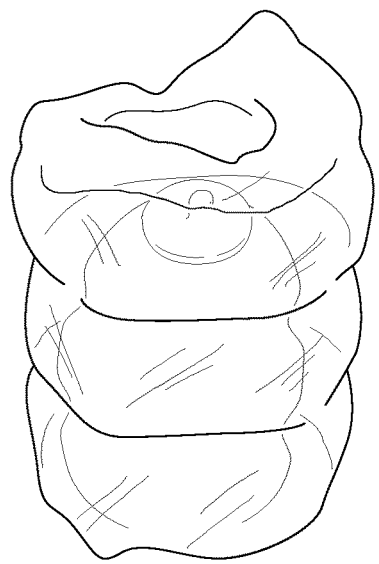
Figure 5C:
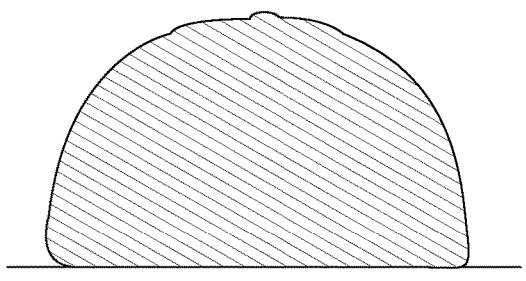
Figure 5D:
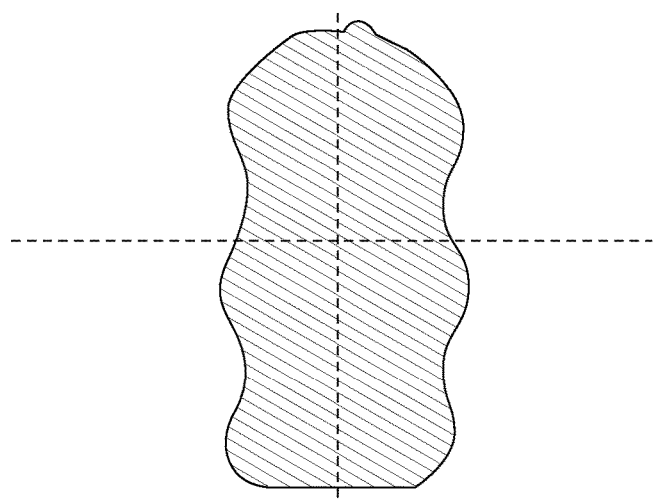

The present invention also relates to the use of a breast fixation device for immobilizing and elongating a human breast during imaging. In one embodiment, a breast fixation device is used as described in U.S. Patent Publication No. 2015/0272682, incorporated herein by reference in its entirety. In one embodiment, the breast fixation device is a generally cylindrical inflatable enclosure that wraps around the breast tissue. In another embodiment, the breast fixation device is composed of multiple rings that are placed around the breast tissue and inflated. In a further embodiment, the breast fixation device consists of multiple inflatable fingers which drape around the breast tissue and then squeeze the breast tissue into an elongated position as they are inflated. In one embodiment, any fixation device that can hold breast tissue in an elongated position can be used. One exemplary embodiment of a fixation device in use is shown in FIG. 5B. The fixation device holds the breast tissue in a fixed elongated position for imaging, as shown in FIG. 5D.

Method of Use

The present invention also relates to methods of using and operating a CT scanner to acquire a CT image of a region of interest of a subject, the scanner being operable to generate x-rays from a source having at least one emission point and having a detector array that cooperates with the X-ray source to define a field of view for the scanner. In one embodiment, scanner is able to take images of a breast of a subject in a supine position.

Figure 3:
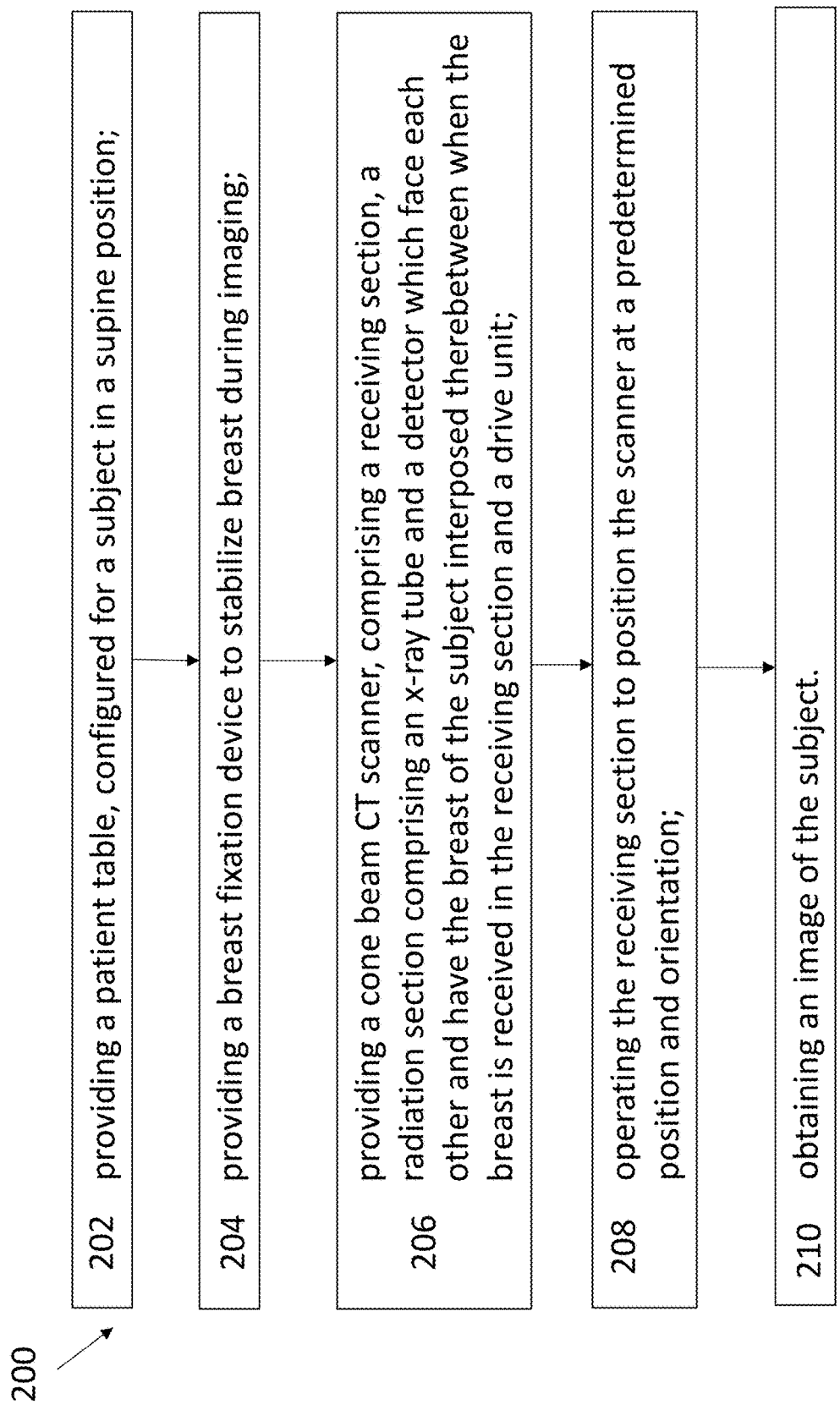
FIG. 3 is a flowchart depicting an exemplary method of imaging breast tissue using an exemplary supine cone beam CT scanner of the present invention.

Referring now to FIG. 3, an exemplary method 200 of using a cone beam CT scanner is depicted. Method 200 begins with step 202, wherein a patient table, configure for a subject in a supine position is provided. In step 204, a breast fixation device to stabilize breast during imaging is provided. In step 206, a cone beam CT scanner, comprising a receiving section, a radiation section comprising an x-ray tube and a detector which face each other and have the receiving section interposed therebetween and a drive unit is provided. In step 208, the receiving section is operated to position the scanner at a predetermined position and orientation. In step 210, an image of the subject is obtained.

In one aspect of the present invention, a method for position detection using a tracking system is provided. The scanner for carrying out the method has at least one marker and is essentially passive, which is coded with information regarding its position. The tracker system may comprise a camera to record the images of markers. The tracking system may be used to calculate the relative position of the scanner within the room, or relative to the patient table, during some or all phases of the scan. Relative position data may in turn be used to calculate the absolute position of an area of interest within the scanned tissue. In some embodiments, a method of the invention includes calculating the absolute position of an area of interest based on a calculated relative position of the scanner, and applying a treatment to the area of interest using a separate instrument within the room, the instrument being also relatively oriented with respect to the patient table.

With the disclosed position calculation steps, methods of the present invention may be used to precisely apply treatments to a particular tissue area identified by a contemporaneous scan.

In one embodiment, the desired location at which the region of interest is positioned is substantially centered along a rotational axis of the scanner.

In one embodiment, the drive unit is operative to control the position and orientation of the receiving section in a fully automatic mode, or in a semi-automatic mode, responsive to input data from an operator.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Optimization of a Breast Immobilization Soft Robot for Supine Breast Setup In this experimental example, a prototypical soft robot device is developed with three rows and six columns for a total of 18 air chambers using a heat press method. Chambers in the same row are connected to the same one-way valve, which is then connected to the same air inlet of a digital pump. All chambers are inflated simultaneously to support and immobilize the breast. As shown in FIG. 5A and FIG. 5B, a deformable silicone breast phantom is set up in the supine position with or without using the prototype.

Compared with its natural shape, the immobilized breast phantom is elongated against gravity, increasing the average breast tissue voxel distance to the base by 2.36 times and simultaneously reducing the variation in tangential radiological pathlengths. This single-gait design shows the feasibility, but the device does not have the flexibility to control the breast shape for different patients with different tissue mechanical properties. To gain the capacity of controlling the shape of individual breasts for optimal radiotherapy dosimetry, a mechanically realistic breast phantom is developed.

Fabrication of Mechanically Realistic Full-Thorax Breast Phantoms

Existing breast phantoms are designed to produce imaging contrast and resolution patterns to test various imaging modalities. Previously the feasibility of the BSSR on healthy human subjects and an isolated breast phantom without underlying tissues was tested. However, to optimize the BSSR, novel mechanically realistic full thorax phantoms with underlying tissues including pectoral muscles, chest wall, ribs and ligaments connecting the soft tissue breast to the supporting tissues as well as the breast are needed.

The bones and muscles are fabricated using a 3D printer and tissue mimicking materials. Specifically, a stereolithography (SLA) printer (Form3L, Formlabs, Somerville, US) is used. Patient CT with stage A-F of ptosis (pendulous breast, FIG. 6 according to the published classification (Kirwan, L., Aesthetic surgery journal, 22(4):355-63) is selected as the templates. The CT is segmented into the muscles, bones, glandular tissues, fat, and skin. The ligaments that cannot be identified based on the CT are generated according to common human anatomy. The bones and muscles are fabricated using the 3D printer. The bones are made of ceramic resins, and the muscles are made of flexible resins (Formlabs). In a smaller format, the same method is used to fabricate a non-human primate phantom for dosimetry purposes with realistic bone, elastic muscles, and other soft tissues (FIG. 6A, FIG. 6B). To fabricate the phantom breast, a mold is made for the glandular and fat tissues based on the CT. Soft silicone gels (Ecoflex, Smooth-on, Macungie, PA) are molded and glued to the underlying 3D printed chest wall. The skin is made using a similar method with two 3D printed shell molds and glued to the fatty and glandular tissues. The gel density is reduced for more pendulous breasts.

Figure 7:
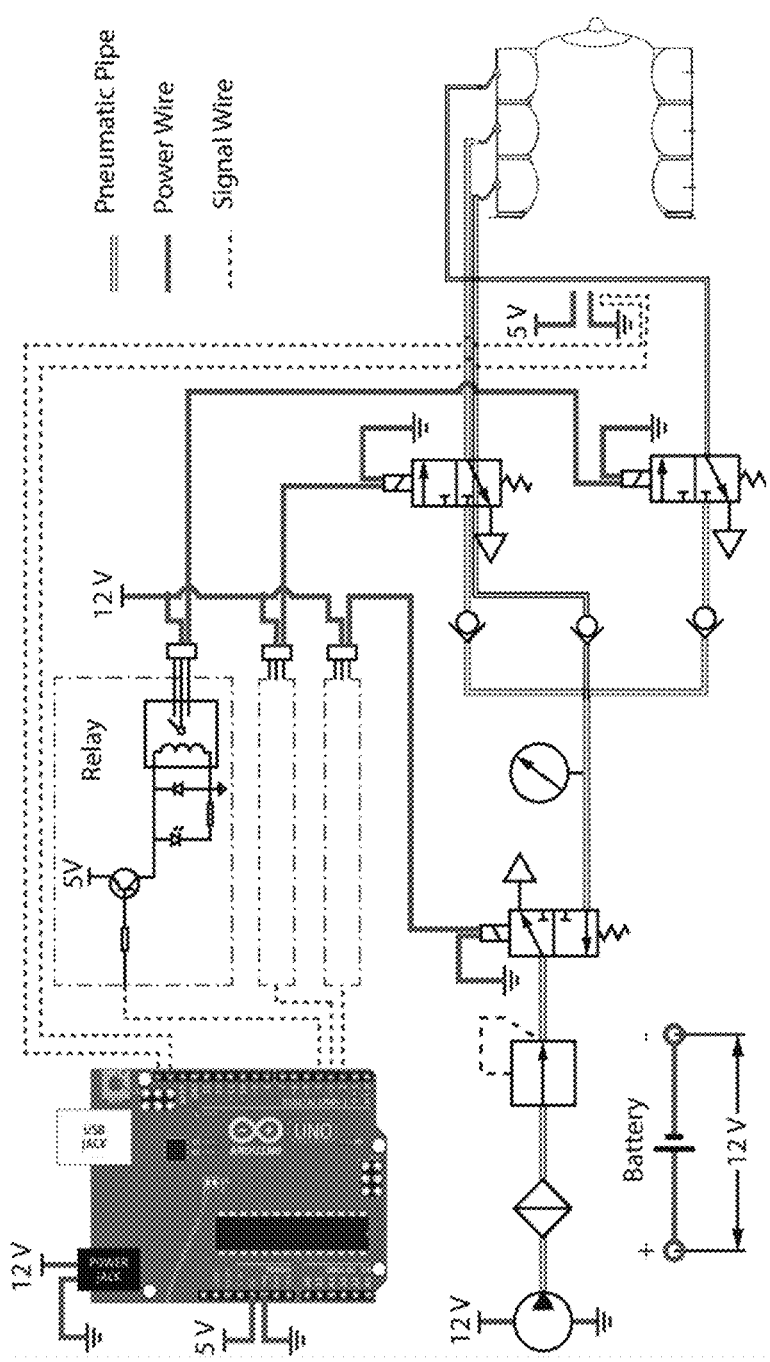
FIG. 7 depicts an exemplary control circuit loop for the new breast setup soft robot (BSSR).

Development of a Multi-Gait Soft Robot for Improved Reproducibility, Stability, and Usability A multi-gait BSSR with increased number of independent movements is developed. Sequential inflation and deflation operation is able to more effectively shape the breast tissues for more desirable radiation dosimetry. A similar implementation of the soft robot is previously reported to mimic the peristaltic motion of the esophagus that performs the swallowing function (M. Z. et al., 2017, IEEE/ASME Transactions on Mechatronics, 22(1):91-8). FEA is performed in parallel to optimize the number of rows and columns of chambers of BSSR, as well as the actuating sequence using the method outlined in (Hasse, K. et al., 2016, Medical Physics, 43(3):1299-311; Martinez, R. V. et al., 2013, Advanced Materials, 25(2):205-12. In this exemplary system, a closed-loop control circuit is adopted as shown in FIG. 7 of the differential drive soft robot (Wu, P. et al., 2018, Soft robotics, 5(1):71-80), which consists of a DC 12V power supply (Eisco labs), an air pump (EW-22222-223, 76 L/min, Cole Palmer, Vernon Hills, IL), reduction valves (UX-98650-32, Cole Palmer), electromagnetic valves (MAC-35A, MAC, Wixom, MI), microcontrollers (Arduino UNO), and the BSSR. The two-position three-way solenoid valves are used to control air chamber actuators' inflation and deflation. Currently, BSSR is fabricated using heat fusion of two layers of membranes (Hotronix Heat Press, BestBlanks). Custom dies are made to vary the number of chambers. Varying pressure and inflation/deflation frequency is tested to determine the optimal sequence for tissue displacement, reproducible and efficient application. The results are evaluated based on the following metrics.

Average Voxel Distance to the Chest Wall

Although the effectiveness of BSSR should be directly determined by the radiotherapy plan dosimetry, the metric varies by patients and types of treatment and thus is impractical here. Alternatively, as a highly correlated and objective metric, in this exemplary system, the average breast voxel distance from the chest wall between the phantoms set up in the supine position is compared with BSSR and in the prone position.

Stability and Repeatability

BSSR is applied on the breast phantoms and then the phantoms are moved to simulate regular patient activities such as sitting up, walking from imaging suite to treatment suite, laying down and rolling from side to side on the couch. Also, the stability is tested with varying skin conditions, including sweating, sebum, and the use of lotion. CT simulator is used to image the breast phantom with such maneuvering, and then compared with the breast external and internal structure surface shapes. BSSR is applied repeatedly after complete removal for 20 times and then, the phantom is CT imaged.

Example 2: Ceiling Mounted Cone Beam CT (CBCT)

The breast immobilization using breast setup soft robot (BSSR) (described in U.S. Patent Publication No. US 2015/0272682 A1) affords many advantages of treating patients in the supine position. However, for patient applications, the treatment accuracy benefits from additional imaging for registration, adaptive planning, and other purposes. The supine CT system of this exemplary system differs from existing dedicated prone breast CTs for its novel functionalities. First, the CT needs to achieve a balance between chest wall coverage and patient comfort. To do so, the system needs to be sufficiently flexible for varying patient chest wall slopes. Second, the system needs to be compatible with existing treatment modalities, e.g., C-arm gantry, CyberKnife, and proton systems, to broaden its impact. Third, the CT images need to be accurately registered to the room coordinates for quantitative treatment intervention.

Optimization of the CT Geometry to Maximize Its Coverage and Accessibility

Figure 4:
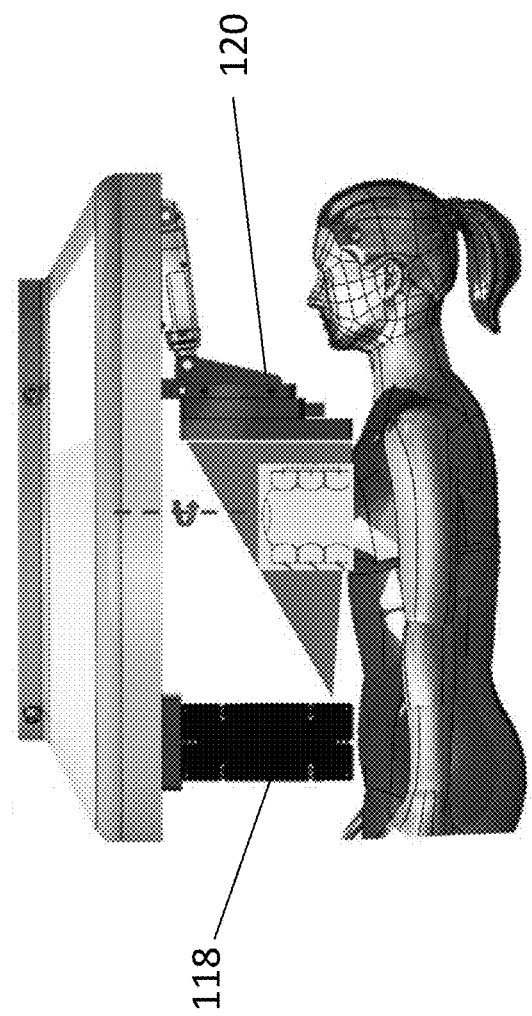
FIG. 4 depicts a side view of an exemplary supine breast CT for taking breast radiographs with the use of a breast fixation device.

The supine breast CT gantry (FIG. 1 and FIG. 4) is ceiling mounted using an LC3 vertical lifting column (LINAK, Denmark). LC3 is a medical degree column that can support up to 6000 N in the payload. It has a high bending moment, high speed, and safety factor of 5 in the push and pull. The column is hydraulically driven and responds to human force guidance and feedback for CT gantry placement. The tuning of the attitude angle of the CBCT scanner is performed using the motion platform with two degrees of freedom including a fixed platform, a moving platform, a supporting column, a telescoping cylinder, and three Hooke hinges. The spatial pitch and roll angles of the moving platform are controlled by the extension and retraction of the two telescoping cylinders and satellite roller screws. The stability of the spatial attitude is achieved using the brake to lock the connecting bar lengths of the telescoping cylinder after the manual tuning of the platform to match the patient chest wall slope. The key to maintaining the stability of the platform is the accurate control on the rigidity of the telescoping cylinder and gaps among the Hooke hinges.

A notch is designed in the CBCT gantry cover for the head to avoid the uncomfortable patient head extension (FIG. 2A). The notch allows the detector to pass but block the X-ray tube, resulting in a 240° scanning angle that produces sufficient data for CT reconstruction.

Development of Optical Tracking of the CT for Accurate Registration of the Breast CT with the Treatment Coordinate Due to the degrees of freedom offered by the ceiling mounted CT and the cumulative error based on motor encoders alone, a position tracking system reference to the static room coordinates is essential. In the field of robotic surgery, a well-established method is stereoscopic optical tracking, which is adopted to locate the ceiling mounted CBCT. A popular optical tracking system, the Polaris Vega® (NDI, Canada) is used in this exemplary system. The Polaris Vega can locate passive and active markers at 60 Hz. Three cross-type optical reflectors are rigidly attached to a round baseplate the same size as the baseplate of the CBCT. The three markers provide X, Y, Z, yaw, pitch and roll of the baseplate, which then determines the origin and orientation of the CT images acquired on such a system. The same weight and weight distribution as the CBCT is attached to the base plate to mimic the mechanical load closely and allow parallel mechanical testing. Throughout the study, errors are calculated as the difference between the coordinates measured by Polaris Vega and the mechanical reference, which is established as follows.

Four laser pointers are fixed to the baseplate. The laser points are placed to aim at the four walls, where rigid plates are mounted to allow marking. One hundred unique positions are created to represent the typical positions of the CBCT and their respective laser markers on the wall places are labeled to represent the CBCT scanner locations relative to the room coordinates. The CBCT baseplate locations are then compared with the Polaris Vega reading. The accuracy and precision are calculated as the average and standard deviation of the errors. For comparison with other results, RMS errors are also calculated.

Example 3: Development of a Versatile Plug-and-Play Reconstruction Algorithm for Extremely Low and Low Dose Breast CT Both the ceiling mounted CBCT mechanical operability and the patient benefit from low dose CT. In modern iterative CT reconstruction, a regularization term is added in the cost function that exploits the human image properties. A common regularization term is total variation that encourages image piece-wise smoothness and at the same time preserve image edges. However, simultaneous improvements in contrast, resolution and noise suppression are challenging, if not impossible, with this type of regularization.

The Block-Matching 3D-transform shrinkage (BM3D) algorithm is a denoising algorithm that was recently proposed and achieved superior image noise suppression relative to local denoising methods (Lebrun, M. 2012, Image Process Line, 2:175-213; Dabov, K. et al., 2007, IEEE T Image Process, 16(8):2080-95). In a naïve fashion, BM3D was applied directly on the CT projection or reconstructed CT images (Sheng, K. et al., 2014, Medical Physics, 41(10); Trinh, H. et al., 2011, Journal of electronic science and technology, 10(2):1-6; Kang, D. et al., 2013, Medical Imaging: Image processing, 8669) as a preprocessing or postprocessing (BM3D post-processing method) component separate from the reconstruction. These studies showed superior image resolution preservation to local denoising methods, but the intricate balance between data fidelity and the regularization was not fully exploited as a single optimization problem. In this exemplary system, the BM3D denoising filter is adopted as a regularization term for CT iterative reconstruction, termed BM3D regularization method. The optimization problem is solved using FISTA (Beck, A. et al., 2009, Siam J Imaging Sci., 2(1):183-202). It is shown that low contrast conspicuity could be improved without sacrificing resolution (Lyu, Q. et al., 2018, Medical Physics, 45(6):2603-10; Jin, J. et al., 2016, International journal of radiation oncology, biology, physics, 95(3):1058-66; Sheng, K. et al., 2014, Medical Physics, 41(10):101916). Recently, deep learning has been shown effective to reconstruct low dose CT images, but its convergence has not proved suitable for the CT reconstruction problem. A flexible Plug-and-Play (PnP) framework was proposed in (Venkatakrishnan, S. et al., 2013, IEEE Glob. Conf. Sig., 945-948) that allows to plug in off-the-shelf denoisers to replace a module in the alternating direction method of multipliers (ADMM) algorithm (Boyd, S., 2011, Proc $51^{st}$ IEEE Conf. Decis. Cont., 3(1):1-44) for model-based image denoising problem. The PnP ADMM algorithm does not require formulating the denoiser into an optimization problem. Instead, the denoiser is applied directly as an iteration step. Studies (Venkatakrishnan, S. et al., 2013, IEEE Glob. Conf. Sig., 945-948; Chan, S. H. et al., 2017, IEEE T Comput. Imag., 3(1):84-98; Wang, X. R. et al., 2017, IEEE International Conference on Acoustics, Speech and Signal Processing (Icassp):1323-7; Sreehari, S. et al., 2016, IEEE T Comput. Imag., 2(4):408-23) have shown promising empirical results on Gaussian and Poissonian image restoration problems using the PnP ADMM framework. In this exemplary system, flexible PnP ADMM framework is adopted for CT iterative reconstruction, incorporating state-of-the-art denoisers such as BM3D (Dabov, K. et al., 2007, IEEE T Comput. Imag., 16(8):2080-95), denoising convolutional neural networks (DnCNN) (Zhang, K. et al., 2017, IEEE T Comput. Imag., 26(7):3142-55).

The materials and methods employed in these experiments are now described.

Benchtop CBCT Hardware

Figure 9:
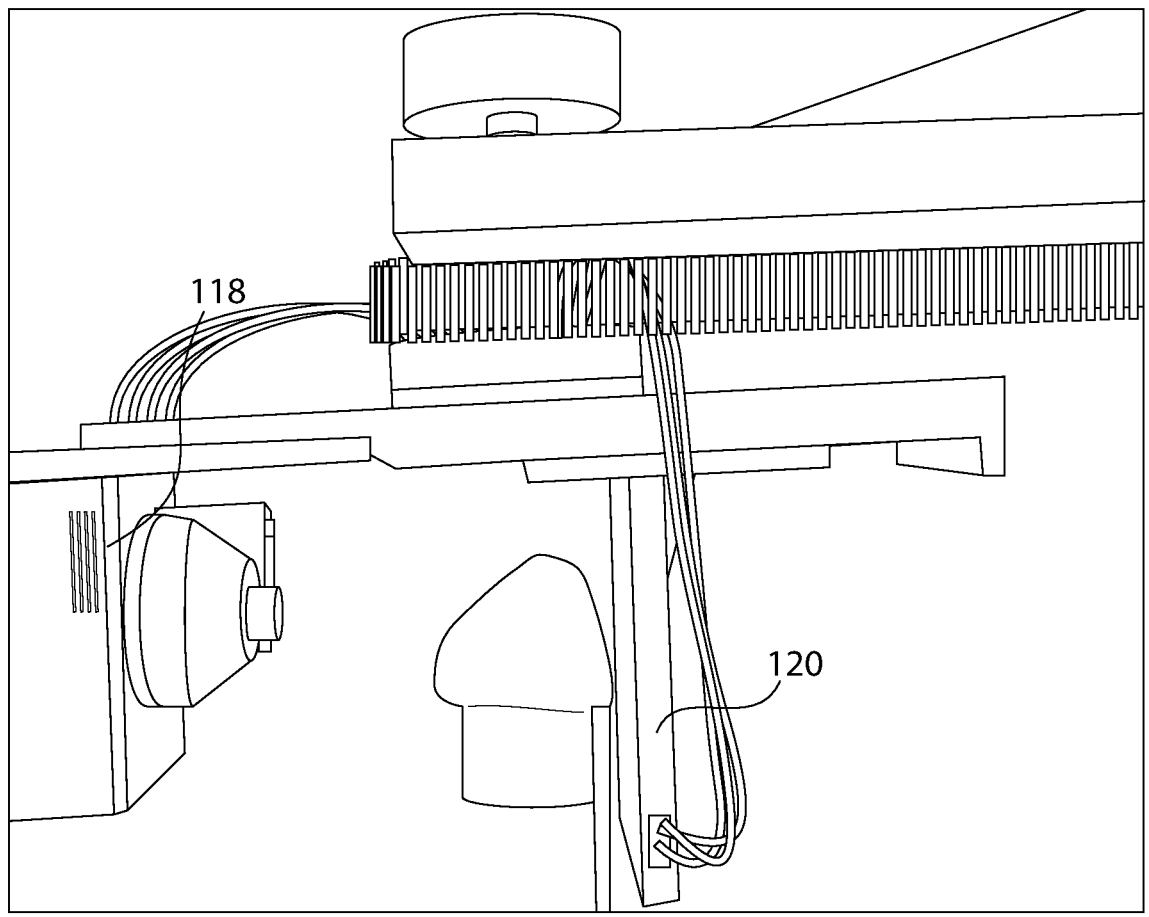
FIG. 9 depicts a current benchtop breast CT with fixed geometry and without the articulated ceiling mounting.

Without interrupting the mechanical structure development as described in Example 1, the existing benchtop CT setup shown in FIG. 9 is used to carry out the experiment. In this setup, the X-ray tube is provided by Toshiba. Key technical specifications include focal spot size 0.4 mm, tube voltage 40-80 kV. The target is oil cooled, and oil cooling tank is air cooled. The headload was initially tested and found that CBCT acquisitions with a 2 minute interval between subsequent scans are sustained, owing to the pulsed X-ray tube. The flat panel detector is provided by CareRay with the following specifications. The active area is 157.7 mm×157.7 mm with a pixel array of 1024×1024. The pixel size is 154 µm. The detector frame rate is 30 f/s at full resolution. The scanning geometry: SID: 278 mm, SAD: 203 mm. The field-of-view is 10 cm or approximately 1.5 liters in cylindrical volume with BSSR, which is expected to fit over 99% of the patients (Wade, T. D. et al., 2010, the official journal of the International Society for Twin Studies, 13(5): 450-4). A heterogeneous breast phantom is fabricated with 30 HU difference in the simulated glandular and fat tissues for this study.

Low Dose Reconstruction

The standard breast CT dose is approximately 5 mGy (Boone, J. M. et al., 2001, Radiology, 221(3):657-67; O'Connell A. et al., AJR American journal of roentgenology, 195(2):496-509), and low dose breast CT dose on the order of 1 mGy was demonstrated (Keyrilainen, J. et al., 2008, Radiology, 249(1):321-7; Kalender, W. A. et al., 2012, European radiology, 22(1):1-8). In this exemplary system, it is aimed to achieve ~100 µGy, ~500 µGy and 1 mGy for the whole breast, partial breast, and focal breast cancer imaging applications, respectively. The X-ray tube current is controlled to achieve the doses, which is validated using Monte Carlo and ion chamber measurement as outlined in Boone, J. M. et al., 2001, Radiology, 221(3)657-67_ENREF_57•For CT reconstruction, the PnP ADMM framework is achieved by combining a least square data fidelity term with a regularization term for image smoothness and is solved through the ADMM. The mathematical formulation is provided in the recent publication Lyu, Q. et al., 2019, SPIE Medical Imaging: Image Processing, 10949. An ADMM module is substituted by an off-the-shelf image denoiser. In addition to the BM3D denoiser, deep-learning based denoising filter, such as DnCNN, is incorporated into the PnP ADMM framework as Algorithm 1 and 2 (Table 1).

TABLE 1

Algorithm 1:
Conjugate Gradient algorithm: Solving Wx = d

Initialization: x := 0, r := d, $\rho_0$ := $\|r\|_2^2$
For k = 1, 2, . . . do
  if k = 1
    p := r
  else
    p := r + $(\rho_{k-1}/\rho_{k-2})$p
  end
  u := Wp
  a := $\rho_{k-1}/p^T u$
  x := x + ap
  r := r − au
  $\rho_k$ := $\|r\|_2^2$
end Algorithm 2:
Plug-and-Play ADMM, the plug-in term is denoted by $D_{\sigma k}$ in the box Initialization: $\rho_0$ := 100, η < 1, γ > 1
For k = 1, 2, . . . do $$x_{k+1} := \mathrm{argmin}_x \frac{1}{2}\|Ax - g\|_2^2 + \frac{\rho_k}{2}\|x - (y_k - z_k)\|_2^2$$

$$\sigma_k := \sqrt{\frac{\beta}{\rho_k}}$$

TABLE 1-continued $y_{k+1} := D_{\sigma_k}(x_{k+1} + z_k)$
$z_{k+1} := z_k + x_{k+1} - y_{k+1}$ $$\Delta_{k+1} := \frac{1}{\sqrt{n}}\begin{pmatrix} \|x_{k+1} - x_k\|_2 + \\ \|y_{k+1} - y_k\|_2 + \\ \|y_{k+1} - y_k\|_2 \end{pmatrix}$$

if $\Delta_{k+1} \geq \eta\Delta_k$
  $\rho_{k+1} := \gamma\rho_k$
else
  $\rho_{k+1} := \rho_k$
end
end The DnCNN (Zhang, K. et al., 2017, IEEE T Image Process, 26)7):3141-55) is a trainable end-to-end denoising network that adopts the residual learning formulation to predict a so-called 'residual image' from the noisy image. A clean image is achieved by the subtraction between the noisy data and the residual. The network consists of 17 layers, incorporating convolution, Batch Normalization, and the Rectified Linear Unit (ReLu). The convolutional filters are set to 3×3. Adam algorithm (Kingma, D. et al., 2014, arXiv:14126980) is used to solve the training optimization. Compared with the direct DCNN application, the PnP framework relies less on the quality of the training data due to the remaining fidelity term.

In one aspect of the invention, commercial breast phantoms are used for breast CT and tomosynthesis quality evaluation (Cockmartin, L. et al., 2013, Medical Physics, 40(8):081920). CIRS breast CT phantoms are acquired (Model 020 with heterogeneous tissue equivalent materials and model 021 with contrast and resolution patterns) to test and compare the CT image quality against known ground truths of the phantoms. The reconstruction image quality is evaluated using HU values (within 3%), contrast to noise ratio (CNR), and modulation transfer function (MTF) as outlined in the publication (Sechopoulos, I., 2012, Medical Physics, 39(5):2896-903).

The results of the experiments are now described.

Figures 11A, 11B, 11C, 11D:
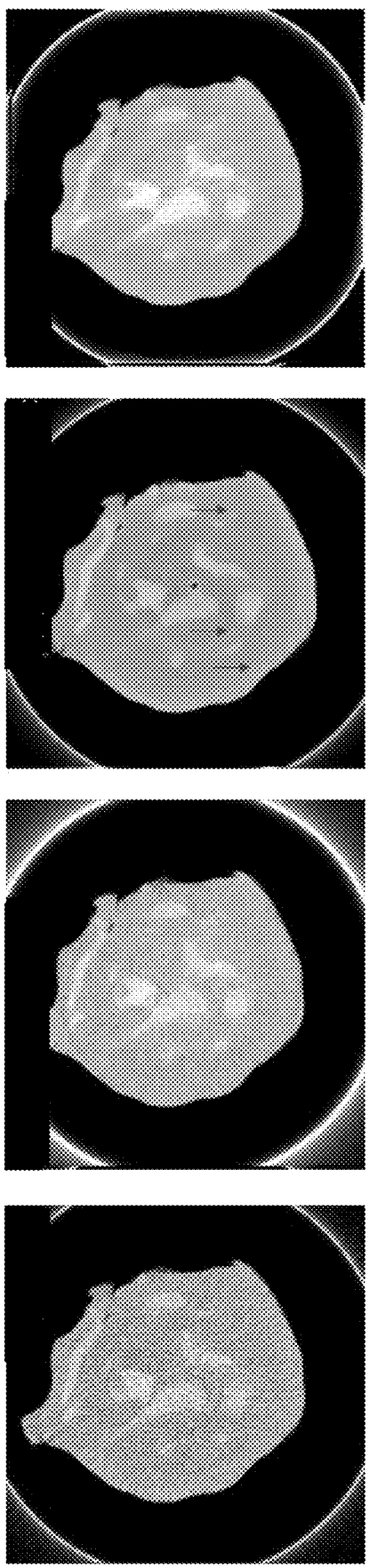
FIG. 11A through FIG. 11D depicts preliminary low dose breast phantom images with ~0.5 mGy imaging dose.

FIG. 10A through FIG. 10D is the reconstructed image with zoomed-in ROI of the ACR phantom using PnP ADMM with BM3D compared with other traditional methods. With reduced image noise, the PnP ADMM (FIG. 10A) clearly distinguished the nine 1p/cm line pairs and achieved a higher image resolution than all other methods. More remarkably, the line pairs are better recovered in the PnP ADMM image (FIG. 10A) with just 5.5% of the imaging dose than the FBP image from standard dose scans (FIG. 10D). DnCNN has already been shown to outperform BM3D for some imaging denoising tasks (Zhang, K. et al., 2017, IEEE T Image Process, 26(7):3142-55). FIG. 11 shows reconstructed breast phantom images with ~0.5 mGy imaging dose. 30 HU difference between the simulated glandular and the fatty tissues can be differentiated. The PnP-ConvNet method result shows greater resilience to artifacts, >3× higher CNR and better detail retention than the naïve ConvNet and TV methods.

Example 4: System Integration and End-To-End Tests with Simulated Breathing Motion A particularly important issue in supine breast radiotherapy is breathing motion, which increases the target localization uncertainty if unaccounted for (Kirby, A. M. et al., 2011, Radiotherapy and oncology: journal of the European Society for Therapeutic Radiology and Oncology, 100(2):221-6). However, it can also be exploited for improved normal organ sparing in the deep inhalation breath hold (DIBH) breast therapy. Therefore, the accuracy of imaging the breast phantom with simulated breathing motion is tested in one aspect of the invention.

Mounting

The benchtop CBCT system is mounted on the mechanical structure relative to a human model as shown in FIG. 9, which is supported by an A-frame. The power supply and data cables to the X-ray tube and the detector is passed through the data conduit of the LC3 column.

Combined imaging and localization accuracy test for breath hold imaging

The subcomponents of the integrated system were tested according to the steps outlined above. In the end-to-end test, the breast phantom was immobilized using BSSR. To account for the breathing motion, the image acquisition was completed in 15 seconds with simulated patient breath-hold. 3D surface cameras (Vision RT custom cameras) were used to monitor the thorax phantom chest wall for breath-hold image and therapy. The phantom was placed on a moving stage (BiSlide 3-axis motion stage). 3D camera was used to quantify the surface location, control the hold position, acquire the image 10 times at the same breathing position as determined by 3D images.

The disclosures of each and every patent, patent application, and publication cited herein are hereby each incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A cone beam CT scanner comprising:
a receiving section configured to receive a breast of the subject whilst in the supine position;
a radiation imaging section comprising an x-ray tube and a detector which face each other and have the receiving section interposed therebetween; and
a drive unit operable to move the receiving section to a position above the breast of the supine subject, suitable for imaging the breast of the subject,
wherein the receiving section comprises:
a lifting column securely attached to the ceiling at a proximal end and perpendicularly attached to top surface of a fixed base at a distal end and is provided with a telescopic mechanism, configured to extend a few inches or several feet;
a moving platform spaced apart from the fixed base in a downward direction by at least two cylinders and a fixed link, wherein each of the cylinders is hingedly connected to the moving platform and provided with a telescoping mechanism, capable of extending the length at least a few inches at a distal end and thereby capable to tilt the moving platform upward and downward; and
a mounting base spaced apart from the moving platform by a slew bearing in a downward direction, wherein rotation of the slew bearing via a driving gear, causes the mounting base to rotate around a vertical axis.

2. The cone beam CT scanner of claim 1, wherein the CT scanner further comprises a cover configured to envelop the scanner.

3. The cone beam CT scanner of claim 2, wherein the cover further comprises a head notch, configured for positioning a head of the subject.

4. The cone beam CT scanner of claim 1, wherein the CT scanner further comprises a tracking system.

5. The cone beam CT scanner of claim 4, wherein the tracking system is selected from the group consisting of: a stereoscopic optical tracker, a stereoscopic video-based tracker, an electromagnetic tracker, a mechanical link-based tracker, a structured-light or laser-based surface scanner, or combinations thereof.

6. The cone beam CT scanner of claim 4, wherein the tracking system comprises at least one passive marker, a control unit and at least one camera.

7. The cone beam CT scanner of claim 1, wherein the x-ray tube is a rotating anode pulsed x-ray source.

8. The cone beam CT scanner of claim 1, wherein the detector is a flat panel detector.

9. A method for breast radiography using a cone beam CT (CBCT) scanner, comprising:
providing a patient table, configured for a subject in a supine position;
providing a breast fixation device to stabilize a subject's breast during imaging;
providing the cone beam CT scanner of claim 1;
operating the drive unit to position the scanner at a predetermined position and orientation; and
obtaining an image of the subject.

10. The method of claim 9, further comprising the step of extending a telescopic mechanism of the drive unit toward the subject.

11. The method of claim 10, wherein the telescopic mechanism comprises a lifting column.

12. The method of claim 9, further comprising changing the position or orientation of the scanner.

13. The method of claim 12, wherein the angle of the scanner relative to the patient table is changed by at least 5 degrees.

14. The method of claim 9, comprising collecting at least 3 images of the subject.

15. The method of claim 14, comprising creating a three-dimensional representation of a tissue of the subject from the at least 3 images.

16. The method of claim 14, wherein the at least 3 images are gathered at a frame rate of between 1 f/s and 50 f/s.

17. The method of claim 16, wherein the at least 3 images are gathered at a frame rate of between 25 f/s and 35 f/s.

18. The method of claim 9, wherein the scanner comprises a notch to accommodate a head of the subject, and further comprising positioning the notch about the head of the subject.

19. The method of claim 9, further comprising calculating a position and orientation of the scanner relative to the patient table.

20. The method of claim 19, further comprising obtaining laser sample data.

21. The method of claim 9, further comprising calculating an absolute position of an area of interest within a tissue of the subject.

22. The method of claim 21, further comprising applying a treatment to the area of interest using a separate instrument.

\* \* \* \* \*